United States Patent
Rey et al.

(10) Patent No.: US 7,033,811 B2
(45) Date of Patent: Apr. 25, 2006

(54) POLYPEPTIDES HAVING XYLOGLUCANASE ACTIVITY AND NUCLEIC ACIDS ENCODING SAME

(75) Inventors: Michael W. Rey, Davis, CA (US); Elizabeth J. Zaretsky, Davis, CA (US); Jeffrey A. Haas, Woodland, CA (US)

(73) Assignee: Novozymes, Inc., Davis, CA (US)

( * ) Notice: Subject to any disclaimer, the term of this patent is extended or adjusted under 35 U.S.C. 154(b) by 262 days.

(21) Appl. No.: 10/420,191

(22) Filed: Apr. 18, 2003

(65) Prior Publication Data

US 2004/0067569 A1    Apr. 8, 2004

Related U.S. Application Data

(60) Provisional application No. 60/373,987, filed on Apr. 19, 2002.

(51) Int. Cl.
  *C12N 9/42*    (2006.01)
  *C12N 1/20*    (2006.01)
  *C12N 15/00*   (2006.01)
  *C11D 3/00*    (2006.01)

(52) U.S. Cl. ............... 435/209; 435/252.3; 435/320.1; 570/226; 570/320; 536/23.2

(58) Field of Classification Search ............... 435/209, 435/252.3, 320.1; 510/226, 320; 536/23.2
See application file for complete search history.

(56) References Cited

U.S. PATENT DOCUMENTS

2003/0113732 A1*  6/2003  Dunn-Colemen et al. ...... 435/6

FOREIGN PATENT DOCUMENTS

WO      WO 97/14953      4/1997

OTHER PUBLICATIONS

Sequence alignment between Applicants SEQ ID NO.:2 and Dunn-Coleman's SEQ ID NO.: 2.*
Fry et al., 1992 Biochem. J. 82: 821-828.
Hayashi et al., 1989, Annu. Rev. Plant Physiol. Plant Mol. Biol. 40: 139-168.
Vicken et al., Trichoderma viride, 1997, Carbohydrate Research 298: 299-310.
Henrissat, B., 1991, Biochem. J. 280: 309-316.
Henrissat and Bairoch, 1993, Biochem. J. 293- 781-788.
Hasper et al., 2002, Applied and Environmental Microbiology 68: 1556-1560.

* cited by examiner

Primary Examiner—Tekchand Saidha
(74) Attorney, Agent, or Firm—Robert L. Starnes

(57) ABSTRACT

The present invention relates to isolated polypeptides having Family 74 xyloglucanase activity and isolated nucleic acid sequences encoding the polypeptides. The invention also relates to nucleic acid constructs, vectors, and host cells comprising the nucleic acid sequences as well as methods for producing and using the polypeptides.

7 Claims, 7 Drawing Sheets

```
    AATTAGGAGTAGGCTCCGAGACAGACTCTAGCAGTGTCCTCCTCCTCACTGCTTCGTCAT
  1 ------------------------------------------------------------ 60
    TTAATCCTCATCCGAGGCTCTGTCTGAGATCGTCACAGGAGGAGGAGTGACGAAGCAGTA
                                                               M

GAAGGTCTCTCGAGTCCTTGCCCTTGTCCTGGGGGCCGTCATCCCTGCCCATGCTGCCTT
 61 ------------------------------------------------------------ 120
    CTTCCAGAGAGCTCAGGAACGGGAACAGGACCCCCGGCAGTAGGGACGGGTACGACGGAA
      K  V  S  R  V  L  A  L  V  L  G  A  V  I  P  A  H  A  A  F

TTCATGGAAGAACGTCAAGCTCGGCGGCGGCGGCGGCTTCGTCCCCGGCATCATCTTCCA
121 ------------------------------------------------------------ 180
    AAGTACCTTCTTGCAGTTCGAGCCGCCGCCGCCGCCGAAGCAGGGGCCGTAGTAGAAGGT
      S  W  K  N  V  K  L  G  G  G  G  F  V  P  G  I  I  F  H

TCCCAAGACAAAAGGCGTAGCATATGCACGAACAGATATTGGCGGGCTGTACCGCCTCAA
181 ------------------------------------------------------------ 240
    AGGGTTCTGTTTTCCGCATCGTATACGTGCTTGTCTATAACCGCCCGACATGGCGGAGTT
      P  K  T  K  G  V  A  Y  A  R  T  D  I  G  G  L  Y  R  L  N

CGCCGACGACTCATGGACCGCCGTCACGGATGGGATTGCTGATAATGCCGGCTGGCACAA
241 ------------------------------------------------------------ 300
    GCGGCTGCTGAGTACCTGGCGGCAGTGCCTACCCTAACGACTATTACGGCCGACCGTGTT
      A  D  D  S  W  T  A  V  T  D  G  I  A  D  N  A  G  W  H  N

CTGGGGCATCGACGCTGTTGCGCTTGATCCGCAGGACGATCAAAAGGTGTATGCCGCAGT
301 ------------------------------------------------------------ 360
    GACCCCGTAGCTGCGACAACGCGAACTAGGCGTCCTGCTAGTTTTCCACATACGGCGTCA
      W  G  I  D  A  V  A  L  D  P  Q  D  D  Q  K  V  Y  A  A  V

CGGCATGTATACGAACAGCTGGTCTGTGATGTCTCTCAGATCTAGACCTATGATTGGACG
361 ------------------------------------------------------------ 420
    GCCGTACATATGCTTGTCGACCAGACACTACAGAGAGTCTAGATCTGGATACTAACCTGC
      G  M  Y  T  N  S  W  ------------------------------------

CTGACATTGGCCATATATAGGGATCCGAGTAATGGAGCCATCATTCGCTCGTCAGACCGC
421 ------------------------------------------------------------ 480
    GACTGTAACCGGTATATATCCCTAGGCTCATTACCTCGGTAGTAAGCGAGCAGTCTGGCG
      ------------------D  P  S  N  G  A  I  I  R  S  S  D  R

GGCGCAACGTGGTCCTTCACCAACTTGCCCTTCAAAGTCGGGGGTAACATGCCAGGACGC
481 ------------------------------------------------------------ 540
    CCGCGTTGCACCAGGAAGTGGTTGAACGGGAAGTTTCAGCCCCCATTGTACGGTCCTGCG
      G  A  T  W  S  F  T  N  L  P  F  K  V  G  G  N  M  P  G  R

GGAGCCGGAGAGCGTCTGGCTGTCGATCCGGCCAACTCCAACATCATCTACTTTGGTGCT
541 ------------------------------------------------------------ 600
    CCTCGGCCTCTCGCAGACCGACAGCTAGGCCGGTTGAGGTTGTAGTAGATGAAACCACGA
      G  A  G  E  R  L  A  V  D  P  A  N  S  N  I  I  Y  F  G  A
```

Fig. 1A

```
      CGCTCAGGAAACGGCCTCTGGAAGTCTACGGACGGCGGCGTGACCTTTTCCAAGGTCTCG
601   ---------+---------+---------+---------+---------+---------+  660
      GCGAGTCCTTTGCCGGAGACCTTCAGATGCCTGCCGCCGCACTGGAAAAGGTTCCAGAGC

R  S  G  N  L  W  K  S  T  D  G  G  V  T  F  S  K  V  S

TCGTTCACGGCAACTGGGACGTACATCCCAGACCCGAGTGATTCCAACGGCTACAACAGC
661   ---------+---------+---------+---------+---------+---------+  720
      AGCAAGTGCCGTTGACCCTGCATGTAGGGTCTGGGCTCACTAAGGTTGCCGATGTTGTCG

S  F  T  A  T  G  T  Y  I  P  D  P  S  D  S  N  G  Y  N  S

GACAAGCAAGGACTCATGTGGGTTACGTTCGACTCAACCAGCAGCACGACCGGGGGAGCC
721   ---------+---------+---------+---------+---------+---------+  780
      CTGTTCGTTCCTGAGTACACCCAATGCAAGCTGAGTTGGTCGTCGTGCTGGCCCCCTCGG

D  K  Q  G  L  M  W  V  T  F  D  S  T  S  S  T  T  G  G  A

ACGTCTCGTATCTTTGTTGGCACGGCTGATAACATCACTGCTTCAGTCTATGTGAGCACG
781   ---------+---------+---------+---------+---------+---------+  840
      TGCAGAGCATAGAAACAACCGTGCCGACTATTGTAGTGACGAAGTCAGATACACTCGTGC

T  S  R  I  F  V  G  T  A  D  N  I  T  A  S  V  Y  V  S  T

AATGCCGGCTCCACGTGGAGTGCTGTACCGGGGCAGCCAGGGAAATACTTTCCTCACAAG
841   ---------+---------+---------+---------+---------+---------+  900
      TTACGGCCGAGGTGCACCTCACGACATGGCCCCGTCGGTCCCTTTATGAAAGGAGTGTTC

N  A  G  S  T  W  S  A  V  P  G  Q  P  G  K  Y  F  P  H  K

GCGAAACTGCAGCCAGCAGAGAAGGCCTTGTATCTGACCTATTCCGATGGCACAGGGCCG
901   ---------+---------+---------+---------+---------+---------+  960
      CGCTTTGACGTCGGTCGTCTCTTCCGGAACATAGACTGGATAAGGCTACCGTGTCCCGGC

A  K  L  Q  P  A  E  K  A  L  Y  L  T  Y  S  D  G  T  G  P

TATGATGGCACACTTGGCTCAGTGTGGAGGTACGACATTGCAGGGGGAACTTGGAAAGAC
961   ---------+---------+---------+---------+---------+---------+  1020
      ATACTACCGTGTGAACCGAGTCACACCTCCATGCTGTAACGTCCCCCTTGAACCTTTCTG

Y  D  G  T  L  G  S  V  W  R  Y  D  I  A  G  G  T  W  K  D

ATCACCCCTGTCTCTGGATCAGATCTATACTTTGGCTTTGGCGGCCTTGGCCTCGATTTG
1021  ---------+---------+---------+---------+---------+---------+  1080
      TAGTGGGGACAGAGACCTAGTCTAGATATGAAACCGAAACCGCCGGAACCGGAGCTAAAC

I  T  P  V  S  G  S  D  L  Y  F  G  F  G  G  L  G  L  D  L

CAAAAGCCAGGAACCCTTGTTGTTGCTTCTTTGAACTCTTGGTGGCCAGATGCTCAGCTG
1081  ---------+---------+---------+---------+---------+---------+  1140
      GTTTTCGGTCCTTGGGAACAACAACGAAGAAACTTGAGAACCACCGGTCTACGAGTCGAC

Q  K  P  G  T  L  V  V  A  S  L  N  S  W  W  P  D  A  Q  L

TTTCGGTCGACCGACTCTGGGACAACATGGAGCCCGATCTGGGCGTGGGCGAGCTATCCG
1141  ---------+---------+---------+---------+---------+---------+  1200
      AAAGCCAGCTGGCTGAGACCCTGTTGTACCTCGGGCTAGACCCGCACCCGCTCGATAGGC
```

ACTGAGACCTATTACTACAGCATCTCAGTGAGTCACTCTTAACGATCCGATGCGAATGGC
     1201 ---------+---------+---------+---------+---------+---------+ 1260
          TGACTCTGGATAATGATGTCGTAGAGTCACTCAGTGAGAATTGCTAGGCTACGCTTACCG

T   E   T   Y   Y   Y   S   I   S   -------------------------------

ACTGACTCTGCTTCAAGACTCCCAAAGCACCGTGGATCAAGAACAACTTTATCGATGTGA
     1261 ---------+---------+---------+---------+---------+---------+ 1320
          TGACTGAGACGAAGTTCTGAGGGTTTCGTGGCACCTAGTTCTTGTTGAAATAGCTACACT

-----------------T   P   K   A   P   W   I   K   N   N   F   I   D   V   T

CGAGCGAGTCACCGTCCGATGGTCTCATCAAGCGCCTCGGCTGGATGATTGAGTCTCTCG
     1321 ---------+---------+---------+---------+---------+---------+ 1380
          GCTCGCTCAGTGGCAGGCTACCAGAGTAGTTCGCGGAGCCGACCTACTAACTCAGAGAGC

S   E   S   P   S   D   G   L   I   K   R   L   G   W   M   I   E   S   L   E

AGATTGACCCAACCGACAGCAACCACTGGCTCTACGGCACCGGAATGACAATCTTTGGCG
     1381 ---------+---------+---------+---------+---------+---------+ 1440
          TCTAACTGGGTTGGCTGTCGTTGGTGACCGAGATGCCGTGGCCTTACTGTTAGAAACCGC

I   D   P   T   D   S   N   H   W   L   Y   G   T   G   M   T   I   F   G   G

GCCACGATCTCACCAACTGGGACACGCGCCACAATGTGTCAATCCAATCACTGGCAGACG
     1441 ---------+---------+---------+---------+---------+---------+ 1500
          CGGTGCTAGAGTGGTTGACCCTGTGCGCGGTGTTACACAGTTAGGTTAGTGACCGTCTGC

H   D   L   T   N   W   D   T   R   H   N   V   S   I   Q   S   L   A   D   G

GCATCGAGGAATTCTCCGTCCAGGACCTGGCCTCTGCACCCGGCGGAAGCGAGCTATTGG
     1501 ---------+---------+---------+---------+---------+---------+ 1560
          CGTAGCTCCTTAAGAGGCAGGTCCTGGACCGGAGACGTGGGCCGCCTTCGCTCGATAACC

I   E   E   F   S   V   Q   D   L   A   S   A   P   G   G   S   E   L   L   A

CCGCAGTCGGAGACGACAACGGCTTCACCTTTGCCAGCAGAAACGACCTCGGGACATCGC
     1561 ---------+---------+---------+---------+---------+---------+ 1620
          GGCGTCAGCCTCTGCTGTTGCCGAAGTGGAAACGGTCGTCTTTGCTGGAGCCCTGTAGCG

A   V   G   D   D   N   G   F   T   F   A   S   R   N   D   L   G   T   S   P

CGCAGACGGTCTGGGCAACGCCCACATGGGCCACCTCGACGAGCGTCGACTACGCCGGGA
     1621 ---------+---------+---------+---------+---------+---------+ 1680
          GCGTCTGCCAGACCCGTTGCGGGTGTACCCGGTGGAGCTGCTCGCAGCTGATGCGGCCCT

Q   T   V   W   A   T   P   T   W   A   T   S   T   S   V   D   Y   A   G   N

ACTCGGTCAAGAGCGTCGTCCGCGTCGGCAACACCGCCGGCACGCAACAGGTGGCCATCT
     1681 ---------+---------+---------+---------+---------+---------+ 1740
          TGAGCCAGTTCTCGCAGCAGGCGCAGCCGTTGTGGCGGCCGTGCGTTGTCCACCGGTAGA

S   V   K   S   V   V   R   V   G   N   T   A   G   T   Q   Q   V   A   I   S

CGTCCGACGGCGGCGCGACGTGGAGCATCGACTACGCGGCCGACACGTCCATGAACGGCG
     1741 ---------+---------+---------+---------+---------+---------+ 1800
          GCAGGCTGCCGCCGCGCTGCACCTCGTAGCTGATGCGCCGGCTGTGCAGGTACTTGCCGC
```

GCACGGTGGCCTATTCGGCCGACGGCGACACGATCCTCTGGTCGACCGCCTCGTCCGGCG
1801    ---------+---------+---------+---------+---------+---------+ 1860
        CGTGCCACCGGATAAGCCGGCTGCCGCTGTGCTAGGAGACCAGCTGGCGGAGCAGGCCGC

T   V   A   Y   S   A   D   G   D   T   I   L   W   S   T   A   S   S   G   V

TGCAGCGCTCGCAGTTCCAGGGCAGCTTTGCCTCCGTCTCGAGCCTGCCCGCGGGCGCCG
1861    ---------+---------+---------+---------+---------+---------+ 1920
        ACGTCGCGAGCGTCAAGGTCCCGTCGAAACGGAGGCAGAGCTCGGACGGGCGCCCGCGGC

Q   R   S   Q   F   Q   G   S   F   A   S   V   S   S   L   P   A   G   A   V

TCATCGCCTCGGACAAGAAGACCAACAGCGTCTTCTACGCCGGCTCCGGATCGACCTTTT
1921    ---------+---------+---------+---------+---------+---------+ 1980
        AGTAGCGGAGCCTGTTCTTCTGGTTGTCGCAGAAGATGCGGCCGAGGCCTAGCTGGAAAA

I   A   S   D   K   K   T   N   S   V   F   Y   A   G   S   G   S   T   F   Y

ACGTCAGCAAGGACACCGGCAGCAGCTTCACGCGCGGGCCCAAGCTGGGCAGCGCAGGGA
1981    ---------+---------+---------+---------+---------+---------+ 2040
        TGCAGTCGTTCCTGTGGCCGTCGTCGAAGTGCGCGCCCGGGTTCGACCCGTCGCGTCCCT

V   S   K   D   T   G   S   S   F   T   R   G   P   K   L   G   S   A   G   T

CGATCCGGGATATCGCTGCTCACCCGACCACCGCGGGCACGTTGTATGTCTCGACCGACG
2041    ---------+---------+---------+---------+---------+---------+ 2100
        GCTAGGCCCTATAGCGACGAGTGGGCTGGTGGCGCCCGTGCAACATACAGAGCTGGCTGC

I   R   D   I   A   A   H   P   T   T   A   G   T   L   Y   V   S   T   D   V

TCGGCATATTCCGCTCCACAGACTCGGGCACGACCTTTGGCCAAGTCTCCACCGCCCTGA
2101    ---------+---------+---------+---------+---------+---------+ 2160
        AGCCGTATAAGGCGAGGTGTCTGAGCCCGTGCTGGAAACCGGTTCAGAGGTGGCGGGACT

G   I   F   R   S   T   D   S   G   T   T   F   G   Q   V   S   T   A   L   T

CCAACACCTACCAGATCGCCCTGGGTGTGGGCTCAGGCTCGAACTGGAACCTGTATGCCT
2161    ---------+---------+---------+---------+---------+---------+ 2220
        GGTTGTGGATGGTCTAGCGGGACCCACACCCGAGTCCGAGCTTGACCTTGGACATACGGA

N   T   Y   Q   I   A   L   G   V   G   S   G   S   N   W   N   L   Y   A   F

TCGGCACCGGCCCGTCAGGGGCTCGCCTCTACGCCAGTGGAGACAGCGGCGCCTCCTGGA
2221    ---------+---------+---------+---------+---------+---------+ 2280
        AGCCGTGGCCGGGCAGTCCCCGAGCGGAGATGCGGTCACCTCTGTCGCCGCGGAGGACCT

G   T   G   P   S   G   A   R   L   Y   A   S   G   D   S   G   A   S   W   T

CGGACATCCAGGGCTCCCAGGGCTTCGGCTCCATCGACAGCACCAAGGTCGCCGGCAGCG
2281    ---------+---------+---------+---------+---------+---------+ 2340
        GCCTGTAGGTCCCGAGGGTCCCGAAGCCGAGGTAGCTGTCGTGGTTCCAGCGGCCGTCGC

```
              GCAGCACCGCCGGGCAAGTCTACGTGGGCACCAACGGCCGGGGCGTCTTTTACGCTCAGG
      2341    ---------+---------+---------+---------+---------+---------+ 2400
              CGTCGTGGCGGCCCGTTCAGATGCACCCGTGGTTGCCGGCCCCGCAGAAAATGCGAGTCC

S  T  A  G  Q  V  Y  V  G  T  N  G  R  G  V  F  Y  A  Q  G

GAACCGTCGGCGGCGGCACGGGCGGGACTTCCTCGTCGACCAAGCAGAGCAGCAGCAGTA
      2401    ---------+---------+---------+---------+---------+---------+ 2460
              CTTGGCAGCCGCCGCCGTGCCCGCCCTGAAGGAGCAGCTGGTTCGTCTCGTCGTCGTCAT

T  V  G  G  T  G  G  T  S  S  S  T  K  Q  S  S  S  S  T

CCTCTTCCGCCAGCTCGAGCACCACGCTGAGGTCGAGCGTTGTATCCACGACCCGGGCTT
      2461    ---------+---------+---------+---------+---------+---------+ 2520
              GGAGAAGGCGGTCGAGCTCGTGGTGCGACTCCAGCTCGCAACATAGGTGCTGGGCCCGAA

S  S  A  S  S  S  T  T  L  R  S  S  V  V  S  T  T  R  A  S

CGACGGTGACTTCGTCGAGGACCAGCTCGGCCGCCGGTCCCACGGGGTCAGGGGTCGCCG
      2521    ---------+---------+---------+---------+---------+---------+ 2580
              GCTGCCACTGAAGCAGCTCCTGGTCGAGCCGGCGGCCAGGGTGCCCCAGTCCCCAGCGGC

T  V  T  S  S  R  T  S  S  A  A  G  P  T  G  S  G  V  A  G

GTCATTATGCTCAGTGCGGAGGGATTGGGTGGACGGGGCCGACGCAGTGTGTGGCGCCGT
      2581    ---------+---------+---------+---------+---------+---------+ 2640
              CAGTAATACGAGTCACGCCTCCCTAACCCACCTGCCCCGGCTGCGTCACACACCGCGGCA

H  Y  A  Q  C  G  G  I  G  W  T  G  P  T  Q  C  V  A  P  Y

ATGTCTGCCAGAAGCAGAATGATTGTGAGTTGCCACCATCTCCATTAGCAGCAGATCCCC
      2641    ---------+---------+---------+---------+---------+---------+ 2700
              TACAGACGGTCTTCGTCTTACTAACACTCAACGGTGGTAGAGGTAATCGTCGTCTAGGGG

V  C  Q  K  Q  N  D  Y----------------------------------

CTTGACTGACTCGGCCGTCACAGATTACTACCAGTGTGTGTGATGCTTGAACTGCCAAGC
      2701    ---------+---------+---------+---------+---------+---------+ 2760
              GAACTGACTGAGCCGGCAGTGTCTAATGATGGTCACACACACTACGAACTTGACGGTTCG

--------------------- Y  Y  Q  C  V  *

TCACGAGGAGAGCTACATACCCCTAGGCTCGCAGTAAAGAGCTCAAGCATCCGAAGAAGC
      2761    ---------+---------+---------+---------+---------+---------+ 2820
              AGTGCTCCTCTCGATGTATGGGGATCCGAGCGTCATTTCTCGAGTTCGTAGGCTTCTTCG

ACTAGTAGTAGAGATCCAGTCAGATAATT
      2821    ---------+---------+--------- 2849
              TGATCATCATCTCTAGGTCAGTCTATTAA
```

Fig. 1E

… # POLYPEPTIDES HAVING XYLOGLUCANASE ACTIVITY AND NUCLEIC ACIDS ENCODING SAME

CROSS-REFERENCE TO RELATED APPLICATION

This application claims the benefit of U.S. Provisional Application No. 60/373,987, filed Apr. 19, 2002, which application is incorporated herein by reference.

BACKGROUND OF THE INVENTION

1. Field of the Invention

The present invention relates to isolated polypeptides having xyloglucanase activity and isolated nucleic acid sequences encoding the polypeptides. The invention also relates to nucleic acid constructs, vectors, and host cells comprising the nucleic acid sequences as well as methods for producing and using the polypeptides.

2. Description of the Related Art

Xyloglucan is a major structural polysaccharide in the primary (growing) cell wall of plants. Xyloglucan is believed to function in the primary wall of plants by cross-linking cellulose-micro fibrils, forming a cellulose-xyloglucan network. This network is considered necessary for the structural integrity of primarty cell walls. Another important function of xyloglucan is to act as a repository for xyloglucan subunit oligosaccharides that are physiologically active regulators of plant cell growth. Xyloglucan subunits may also modulate the action of a xyloglucan endotransglycosylase (XET), a cell wall associated enzyme that has been hypothesized to play a role in the elongation of plant cell walls. Thus, xyloglucan might play a role in wall loosening and consequently cell expansion (Fry et al., 1992, *Biochem. J.* 82: 821–828).

Structurally, xyloglucans consist of a cellulose-like beta-1,4-linked glucose backbone, which is frequently substituted with various side chains. The side chains are composed of xylosyl, galactosyl, fucosyl, and/or arabinosyl residues (Hayashi et al., 1989, *Annu. Rev. Plant Physiol. Plant Mol. Biol.* 40: 139–168). The xyloglucans of most dicotyledonous plants and some monocotyledons and gymnosperms, are highly branched polysaccharides in which approximately 75% of the glucose residues in the backbone bear a glycosyl side chain at O-6. The glycosyl residue attached to the branched glucose residue is invariably alpha-D-xylose. Up to 50% of the side chains in xyloglucans contain more than one residue due to the presence of beta-D-galactose or alpha-L-fucose-(1-2)-beta-D-galactose moieties at O-2 of the xylose residue.

Xyloglucanases hydrolyze the beta-1,4-glycosidic linkages in the backbone of xyloglucan to xyloglucan oligosaccharides. Xyloglucanases generally exhibit minor cellulolytic activity against conventional substrates such as carboxymethycellulose, HE cellulose, and Avicel (microcrystalline cellulose).

Vicken et al. have disclosed the characterization of three endoglucanases (endoglucanases I, IV, and V) from *Trichoderma viride* (1997, *Carbohydrate Research* 298: 299–310). All three endoglucanases have high activity toward cellulose or carboxymethycellulose, but endoglucanase I (belonging to family 5 of glycosyl hydrolases) has essentially no activity toward xyloglucan, while both endoglucanase IV (belonging to family 12 of glycosyl hydrolases) and endoglucanase V (belonging to family 7 of glycosyl hydrolases) have activity against xyloglucan (see Henrissat, B., 1991, *Biochem. J.*, 280: 309–316, and Henrissat and Bairoch, 1993, *Biochem. J.*, 293: 781–788).

WO 97/14953 discloses a xyloglucanase gene (endoglucanase II) cloned from the *Aspergillus aculeatus* and expressed in *Aspergillus oryzae*. The xyloglucanase has high xyloglucanase activity and very little cellulase activity with xyloglucanase activity in the pH range 2.5–6 and optimum activity at pH 3–4. Hasper et al., 2002, *Applied and Environmental Microbiology* 68: 1556–1560, disclose an endoglucanase from *Aspergillus niger* with major activity toward xyloglucan.

It is an object of the present invention to provide improved polypeptides having xyloglucanase activity and nucleic acid encoding the polypeptides.

SUMMARY OF THE INVENTION

The present invention relates to isolated polypeptides having Family 74 xyloglucanase activity selected from the group consisting of:

(a) a polypeptide having an amino acid sequence which has at least 70% identity with amino acids 20 to 838 of SEQ ID NO: 2;

(b) a polypeptide encoded by a nucleic acid sequence which hybridizes under one: medium stringency conditions with (i) nucleotides 115 to 2739 of SEQ ID NO: 1, (ii) the cDNA sequence contained in nucleotides 115 to 2739 of SEQ ID NO: 1, (iii) a subsequence of (i) or (ii) of at least contiguous 100 nucleotides, or (iv) a complementary strand of (i), (ii), or (iii); and (c) a fragment of (a) or (b) having Family 74 xyloglucanase activity.

The present invention also relates to isolated nucleic acid sequences encoding the polypeptides and to nucleic acid constructs, vectors, and host cells comprising the nucleic acid sequences as well as methods for producing and using the polypeptides.

BRIEF DESCRIPTION OF THE FIGURES

FIG. 1 shows the genomic DNA sequence and the deduced amino acid sequence of a *Trichoderma reesei* ATCC 56765 Family 74 xyloglucanase (SEQ ID NOS: 1 and 2, respectively).

DETAILED DESCRIPTION OF THE INVENTION

Polypeptides Having Family 74 Xyloglucanase Activity

Figure 2:
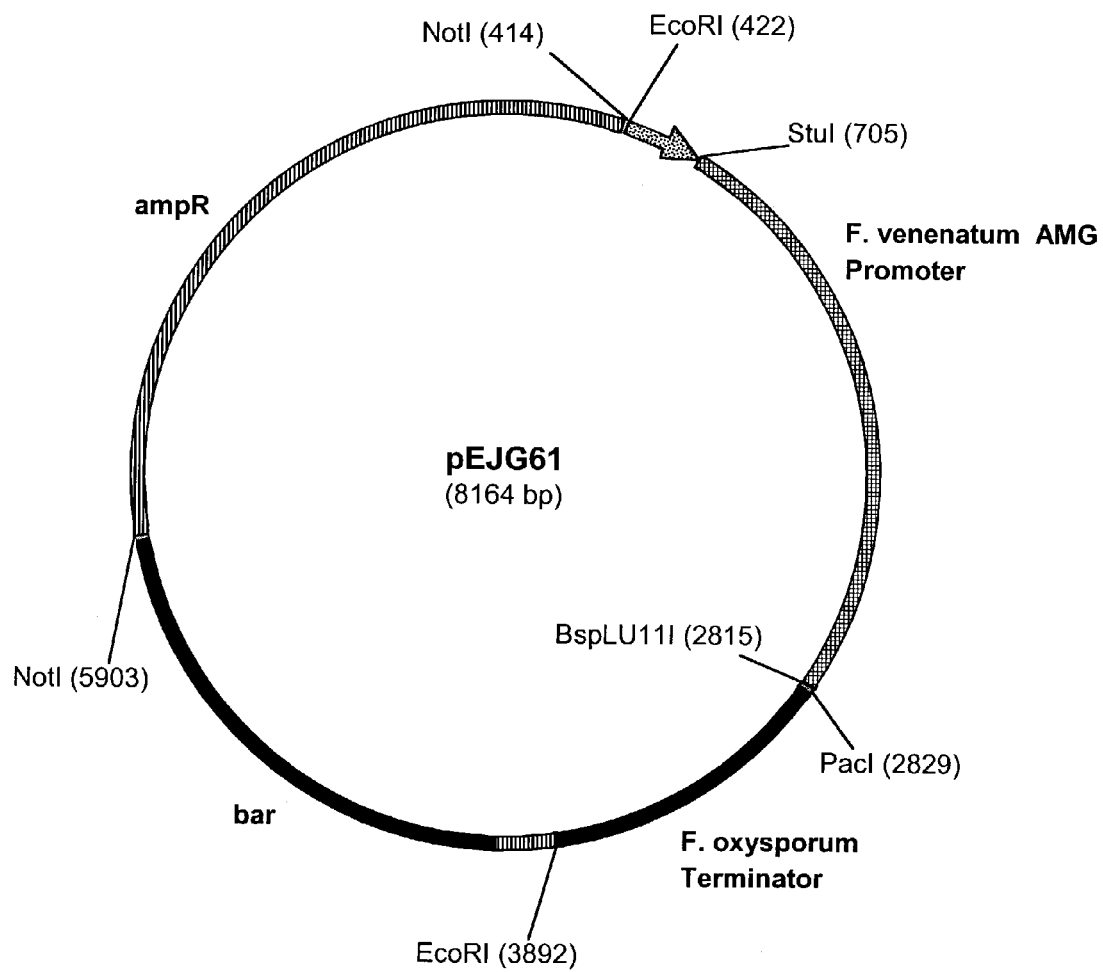
FIG. 2 shows a restriction map of pEJG61.

The present invention relates to isolated Family 74 glycoside hydrolases having xyloglucanase activity selected from the group consisting of: (a) a polypeptide having an amino acid sequence which has at least 70% identity with amino acids 20 to 838 of SEQ ID NO: 2; (b) a polypeptide encoded by a nucleic acid sequence which hybridizes under one: medium stringency conditions with (i) nucleotides 115 to 2739 of SEQ ID NO: 1, (ii) the cDNA sequence contained in nucleotides 115 to 2739 of SEQ ID NO: 1, (iii) a subsequence of (i) or (ii) of at least contiguous 100 nucleotides, or (iv) a complementary strand of (i), (ii), or (iii); and (c) a fragment of (a) or (b) having Family 74 xyloglucanase activity.

For classification of glycoside hydrolases see Coutinho and Henrissat, 1999, in *Recent Advances in Carbohydrate*

*Bioengineering,* H. J. Gilbert, G. Davies, B. Henrissat and B. Svensson eds., The Royal Society of Chemistry, Cambridge, pp. 3–12; and Coutinho and Henrissat, 1999, In *Genetics, Biochemistry and Ecology of Cellulose Degradation,* K. Ohmiya, K. Hayashi, K. Sakka, Y. Kobayashi, S. Karita and T. Kimura eds., Uni Publishers Co., Tokyo, pp. 15–23; Henrissat et al., 1996, *Biochem. J.* 316: 695–696; Davies and Henrissat, 1995, *Structure* 3: 853–859.

Classification of glycoside hydrolases into families is based on amino acid sequence similarities. Because there is a direct relationship between the amino acid sequence of a protein and its folding similarities, such a classification is expected to reflect the structural features of these enzymes better than their substrate specificity. Such a classification system can help to reveal the evolutionary relationships between these enzymes and provide a convenient tool to derive mechanistic information (afmb.cnrs-mrs.fr/CAZY/index.html). The phrase "Family 74 glycoside hydrolases" is defined herein as those glycosyl hydrolases whose catalytic domains have significant similarity to one another. Some members of the Family 74 glycosyl hydrolase include *Aspergillus aculeatus* avicelase III (SwissProt O74170), *Aspergillus niger* endoglucanase C (GenPept AAK77227.1), and *Thermotoga maritima* Cel74 (SwissProt Q9WYE1). Such Family 74 glycosyl hydrolases having xyloglucanase activity will be herein designated "polypeptides having Family 74 xyloglucanase activity."

The term "xyloglucanase activity" is defined herein as an enzyme that hydrolyzes the beta-1,4-glycosidic linkages in the backbone of xyloglucan to xyloglucan oligosaccharides. For purposes of the present invention, xyloglucanase activity is determined according to the procedure described by Lever, 1972, *Analytical Biochemistry* 47: 273–279 where the hydrolysis of xyloglucan is measured at pH 5.0, 50° C. and by detecting generated reducing sugars with p-hydroxy-benzoic acid hydrazide at 410 nm. One unit of xyloglucanase activity is defined as 1.0 μmole of reducing sugar produced per minute at 50° C., pH 5.

In a first embodiment, the present invention relates to isolated polypeptides having an amino acid sequence which has a degree of identity to amino acids 20 to 838 of SEQ ID NO: 2 (i.e., the mature polypeptide) of at least about 70%, preferably at least about 75%, more preferably at least about 80%, even more preferably at least about 85%, even more preferably at least about 90%, most preferably at least about 95%, and even most preferably at least about 97%, which have Family 74 xyloglucanase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 20 to 838 of SEQ ID NO: 2. For purposes of the present invention, the degree of identity between two amino acid sequences is determined by the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

Preferably, the polypeptides of the present invention comprise the amino acid sequence of SEQ ID NO: 2 or an allelic variant thereof; or a fragment thereof that has Family 74 xyloglucanase activity. In a more preferred embodiment, the polypeptide of the present invention comprises the amino acid sequence of SEQ ID NO: 2. In another preferred embodiment, the polypeptide of the present invention comprises amino acids 20 to 838 of SEQ ID NO: 2, or an allelic variant thereof; or a fragment thereof that has Family 74 xyloglucanase activity. In another preferred embodiment, the polypeptide of the present invention comprises amino acids 20 to 838 of SEQ ID NO: 2. In another preferred embodiment, the polypeptide of the present invention consists of the amino acid sequence of SEQ ID NO: 2 or an allelic variant thereof; or a fragment thereof that has Family 74 xyloglucanase activity. In another preferred embodiment, the polypeptide of the present invention consists of the amino acid sequence of SEQ ID NO: 2. In another preferred embodiment, the polypeptide consists of amino acids 20 to 838 of SEQ ID NO: 2 or an allelic variant thereof; or a fragment thereof that has Family 74 xyloglucanase activity. In another preferred embodiment, the polypeptide consists of amino acids 20 to 838 of SEQ ID NO: 2.

A fragment of SEQ ID NO: 2 is a polypeptide having one or more amino acids deleted from the amino and/or carboxyl terminus of this amino acid sequence. Preferably, a fragment contains at least 730 amino acid residues, more preferably at least 760 amino acid residues, and most preferably at least 790 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In a second embodiment, the present invention relates to isolated polypeptides having Family 74 xyloglucanase activity which are encoded by nucleic acid sequences which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) nucleotides 115 to 2739 of SEQ ID NO: 1, (ii) the cDNA sequence contained in nucleotides 115 to 2739 of SEQ ID NO: 1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual,* 2d edition, Cold Spring Harbor, N.Y.). The subsequence of SEQ ID NO: 1 may be at least 100 nucleotides or preferably at least 200 nucleotides. Moreover, the subsequence may encode a polypeptide fragment which has Family 74 xyloglucanase activity. The polypeptides may also be allelic variants or fragments of the polypeptides that have Family 74 xyloglucanase activity.

The nucleic acid sequence of SEQ ID NO: 1 or a subsequence thereof, as well as the amino acid sequence of SEQ ID NO: 2 or a fragment thereof, may be used to design a nucleic acid probe to identify and clone DNA encoding polypeptides having Family 74 xyloglucanase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^3$H, $^{35}$S, biotin, or avidin). Such probes are encompassed by the present invention.

Thus, a genomic DNA or cDNA library prepared from such other organisms may be screened for DNA, which hybridizes with the probes described above and which encodes a polypeptide having Family 74 xyloglucanase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO: 1, its complementary strand, or a subsequence thereof, under very low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID NO: 2, or a subsequence thereof. In another preferred embodiment, the nucleic acid probe is SEQ ID NO: 1. In another preferred embodiment, the nucleic acid probe is the mature polypeptide coding region of SEQ ID NO: 1. In another preferred embodiment, the nucleic acid probe is the nucleic acid sequence contained in plasmid pEJG81 which is contained in *Escherichia coli* NRRL B-30502, wherein the nucleic acid sequence encodes a polypeptide having Family 74 xyloglucanase activity. In another preferred embodiment, the nucleic acid probe is the mature polypeptide coding region contained in plasmid pEJG81 which is contained in *Escherichia coli* NRRL B-30502.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes that are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third embodiment, the present invention relates to variants of the polypeptide having an amino acid sequence of SEQ ID NO: 2 comprising a substitution, deletion, and/or insertion of one or more amino acids.

The amino acid sequences of the variant polypeptides may differ from the amino acid sequence of SEQ ID NO: 2 or the mature polypeptide thereof by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a fourth embodiment, the present invention relates to isolated polypeptides having immunochemical identity or partial immunochemical identity to the polypeptide having the amino acid sequence of SEQ ID NO: 2 or the mature polypeptide thereof. The immunochemical properties are determined by immunological cross-reaction identity tests by the well-known Ouchterlony double immunodiffusion procedure. Specifically, an antiserum containing polyclonal antibodies which are immunoreactive or bind to epitopes of the polypeptide having the amino acid sequence of SEQ ID NO: 2 or the mature polypeptide thereof are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, *A Manual of Quantitative Immunoelectrophoresis*, Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, *Antibodies, A Laboratory Manual*, Cold Spring Harbor Press, Cold Spring Harbor, N.Y.

The polypeptides of the present invention have at least 20%, preferably at least 40%, more preferably at least 60%, even more preferably at least 80%, even more preferably at least 90%, and most preferably at least 100% of the Family 74 xyloglucanase activity of the mature polypeptide of SEQ ID NO: 2.

A polypeptide of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide is secreted extracellularly.

A polypeptide of the present invention may be a bacterial polypeptide. For example, the polypeptide may be a gram positive bacterial polypeptide such as a *Bacillus* polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

A polypeptide of the present invention may be a fungal polypeptide, and more preferably a yeast polypeptide such as a *Candida, Kluyveromyces, Pichia, Saccharomyces, Schizosaccharomyces,* or *Yarrowia* polypeptide; or more preferably a filamentous fungal polypeptide such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* or *Trichoderma* polypeptide.

In a preferred embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* polypeptide.

In another preferred embodiment, the polypeptide is an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa,* or *Penicillium purpurogenum* polypeptide.

In another preferred embodiment, the polypeptide is a *Trichoderma harzianum, Trichoderma koningii, Trichoderma longibrachiatum, Trichoderma reesei,* or *Trichoderma viride* polypeptide.

In a more preferred embodiment, the polypeptide is a *Trichoderma reesei* polypeptide, and most preferably a *Trichoderma reesei* ATCC 56765 polypeptide, e.g., the polypeptide with the amino acid sequence of SEQ ID NO: 2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-xyloglucanase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Sequences

The present invention also relates to isolated nucleic acid sequences which encode a polypeptide of the present invention. In a preferred embodiment, the nucleic acid sequence is set forth in SEQ ID NO: 1. In another more preferred embodiment, the nucleic acid sequence is the sequence contained in plasmid pEJG81 that is contained in *Escherichia coli* NRRL B-30502. In another preferred embodiment, the nucleic acid sequence is the mature polypeptide coding region of SEQ ID NO: 1. In another more preferred embodiment, the nucleic acid sequence is the mature polypeptide coding region contained in plasmid pEJG81 that is contained in *Escherichia coli* NRRL B-30502. The present invention also encompasses nucleic acid sequences which encode a polypeptide having the amino acid sequence of SEQ ID NO: 2 or the mature polypeptide thereof, which differ from SEQ ID NO: 1 by virtue of the degeneracy of the genetic code. The present invention also relates to subsequences of SEQ ID NO: 1 which encode fragments of SEQ ID NO: 2 that have Family 74 xyloglucanase activity.

A subsequence of SEQ ID NO: 1 is a nucleic acid sequence encompassed by SEQ ID NO: 1 except that one or more nucleotides from the 5' and/or 3' end have been deleted. Preferably, a subsequence contains at least 2190 nucleotides, more preferably at least 2280 nucleotides, and most preferably at least 2370 nucleotides.

The present invention also relates to mutant nucleic acid sequences comprising at least one mutation in the mature polypeptide coding sequence of SEQ ID NO: 1, in which the mutant nucleic acid sequence encodes a polypeptide which consists of amino acids 20 to 838 of SEQ ID NO: 2.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of *Trichoderma*, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to the mature polypeptide coding sequence of SEQ ID NO: 1 (i.e., nucleotides 115 to 2739) of at least about 70%, preferably about 75%, preferably about 80%, more preferably about 85%, even more preferably about 90%, most preferably about 95%, and even most preferably about 97% homology, which encode an active polypeptide. For purposes of the present invention, the degree of homology between two nucleic acid sequences is determined by the Wilbur-Lipman method (Wilbur and Lipman, 1983, *Proceedings of the National Academy of Science USA* 80: 726–730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=3, gap penalty=3, and windows=20.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO: 1, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for Family 74 xyloglucanase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

The present invention also relates to isolated nucleic acid sequences encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with the nucleic acid sequence of SEQ ID NO: 1 or its complementary strand; or allelic variants and subsequences thereof (Sambrook et al., 1989, supra), as defined herein.

The present invention also relates to isolated nucleic acid sequences produced by (a) hybridizing a population of DNA under very low, low, medium, medium-high, high, or very high stringency conditions with (i) nucleotides 115 to 2739 of SEQ ID NO: 1, (ii) the cDNA sequence contained in nucleotides 115 to 2739 of SEQ ID NO: 1, (iii) a subsequence of (i) or (ii), or (iv) a complementary strand of (i), (ii), or (iii); and (b) isolating the nucleic acid sequence from the population of DNA. The subsequence is preferably a sequence of at least 100 nucleotides such as a sequence which encodes a polypeptide fragment which has Family 74 xyloglucanase activity.

Methods for Producing Mutant Nucleic Acid Sequences

The present invention further relates to methods for producing a mutant nucleic acid sequence, comprising introducing at least one mutation into the mature polypeptide coding sequence of SEQ ID NO: 1 or a subsequence thereof, wherein the mutant nucleic acid sequence encodes a polypeptide which consists of amino acids 20 to 838 of SEQ ID NO: 2 or a fragment thereof which has Family 74 xyloglucanase activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with Dpnl which is specific for methylated and hemi-methylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence which directly specifies the amino acid sequence of its protein product. The boundaries of a genomic coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Sac-* charomyces cerevisiae galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423–488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

In a preferred embodiment, the signal peptide coding region is nucleotides 59 to 114 of SEQ ID NO: 1 which encode amino acids 1 to 19 of SEQ ID NO: 2.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The present invention also relates to nucleic acid constructs for altering the expression of an endogenous gene encoding a polypeptide of the present invention. The constructs may contain the minimal number of components necessary for altering expression of the endogenous gene. In one embodiment, the nucleic acid constructs preferably contain (a) a targeting sequence, (b) a regulatory sequence, (c) an exon, and (d) a splice-donor site. Upon introduction of the nucleic acid construct into a cell, the construct inserts by homologous recombination into the cellular genome at the endogenous gene site. The targeting sequence directs the integration of elements (a)–(d) into the endogenous gene such that elements (b)–(d) are operably linked to the endogenous gene. In another embodiment, the nucleic acid constructs contain (a) a targeting sequence, (b) a regulatory sequence, (c) an exon, (d) a splice-donor site, (e) an intron, and (f) a splice-acceptor site, wherein the targeting sequence directs the integration of elements (a)–(f) such that elements (b)–(f) are operably linked to the endogenous gene. However, the constructs may contain additional components such as a selectable marker.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell. The activated gene can be further amplified by the inclusion of an amplifiable selectable marker gene in the construct using methods well known in the art (see, for example, U.S. Pat. No. 5,641,670). In another embodiment in which the endogenous gene is altered, expression of the gene is reduced.

The targeting sequence can be within the endogenous gene, immediately adjacent to the gene, within an upstream gene, or upstream of and at a distance from the endogenous gene. One or more targeting sequences can be used. For example, a circular plasmid or DNA fragment preferably employs a single targeting sequence, while a linear plasmid or DNA fragment preferably employs two targeting sequences.

The regulatory sequence of the construct can be comprised of one or more promoters, enhancers, scaffold-attachment regions or matrix attachment sites, negative regulatory elements, transcription binding sites, or combinations of these sequences.

The constructs further contain one or more exons of the endogenous gene. An exon is defined as a DNA sequence which is copied into RNA and is present in a mature mRNA molecule such that the exon sequence is in-frame with the coding region of the endogenous gene. The exons can, optionally, contain DNA which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the nucleic acid sequence encoding the polypeptide or any other element of the vector for integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gen e, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus*, or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a *Candida, Hansenula, Kluyveromyces, Pichia, Saccharomyces, Schizosaccharomyces*, or *Yarrowia* cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium,* or *Trichoderma*.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470–1474. Suitable methods for transforming *Fusarium* species are described by Malardier et al., 1989, *Gene* 78: 147–156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a strain, which in its wild-type form is capable of producing the polypeptide, to produce the polypeptide; and (b) recovering the polypeptide. Preferably, the strain is of the genus *Trichoderma*, and more preferably *Trichoderma reesei*.

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence having at least one mutation in the mature polypeptide coding region of SEQ ID NO: 1, wherein the mutant nucleic acid sequence encodes a polypeptide which consists of amino acids 20 to 838 of SEQ ID NO: 2, and (b) recovering the polypeptide.

The present invention further relates to methods for producing a polypeptide of the present invention comprising (a) cultivating a homologously recombinant cell, having incorporated therein a new transcription unit comprising a regulatory sequence, an exon, and/or a splice donor site operably linked to a second exon of an endogenous nucleic acid sequence encoding the polypeptide, under conditions conducive for production of the polypeptide; and (b) recovering the polypeptide. The methods are based on the use of gene activation technology, for example, as described in U.S. Pat. No. 5,641,670.

In the production methods of the present invention, the cells are cultivated in a nutrient medium suitable for production of the polypeptide using methods known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having Family 74 xyloglucanase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an anti-nutritive factor.

The transgenic plant can be dicotyledonous (a dicot) or monocotyledonous (a monocot). Examples of monocot plants are grasses, such as meadow grass (blue grass, Poa), forage grass such as festuca, lolium, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the $^{35}$S-CaMV promoter may be used (Franck et al., 1980, *Cell* 21: 285–294). Organ-specific promoters may be, for example, a promoter from storage sink tissues such as seeds, potato tubers, and fruits (Edwards & Coruzzi, 1990, *Ann. Rev. Genet.* 24: 275–303), or from metabolic sink tissues such as meristems (Ito et al., 1994, *Plant Mol. Biol.* 24: 863–878), a seed specific promoter such as the glutelin, prolamin, globulin, or albumin promoter from rice (Wu et al., 1998, *Plant and Cell Physiology* 39: 885–889), a *Vicia faba* promoter from the legumin B4 and the unknown seed protein gene from *Vicia faba* (Conrad et al., 1998, *Journal of Plant Physiology* 152: 708–711), a promoter from a seed oil body protein (Chen et al., 1998, Plant and Cell Physiology 39: 935–941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al, 1993, *Plant Physiology* 102: 991–1000, the chlorella virus adenine methyltransferase gene promoter (Mitra and Higgins, 1994, *Plant Molecular Biology* 26: 85–93), or the aldP gene promoter from rice (Kagaya et al., 1995, *Molecular and General Genetics* 248: 668–674), or a wound inducible promoter such as the potato pin2 promoter (Xu et al., 1993, *Plant Molecular Biology* 22: 573–588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15–38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275–281; Shimamoto, 1994, *Current Opinion Biotechnology* 5: 158–162; Vasil et al., 1992, *Bio/Technology* 10: 667–674). An alternative method for transformation of monocots is based on protoplast transformation as described by Omirulleh et al., 1993, *Plant Molecular Biology* 21: 415–428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a polypeptide having Family 74 xyloglucanase activity of the present invention under conditions conducive for production of the polypeptide; and (b) recovering the polypeptide.

Removal or Reduction of Family 74 Xyloglucanase Activity

The present invention also relates to methods for producing a mutant cell of a parent cell, which comprises disrupting or deleting a nucleic acid sequence encoding the polypeptide or a control sequence thereof, which results in the mutant cell producing less of the polypeptide than the parent cell when cultivated under the same conditions.

The construction of strains which have reduced Family 74 xyloglucanase activity may be conveniently accomplished by modification or inactivation of a nucleic acid sequence necessary for expression of the polypeptide having Family 74 xyloglucanase activity in the cell. The nucleic acid sequence to be modified or inactivated may be, for example, a nucleic acid sequence encoding the polypeptide or a part thereof essential for exhibiting Family 74 xyloglucanase activity, or the nucleic acid sequence may have a regulatory function required for the expression of the polypeptide from the coding sequence of the nucleic acid sequence. An example of such a regulatory or control sequence may be a promoter sequence or a functional part thereof, i.e., a part which is sufficient for affecting expression of the polypeptide. Other control sequences for possible modification are described above.

Modification or inactivation of the nucleic acid sequence may be performed by subjecting the cell to mutagenesis and selecting or screening for cells in which the xyloglucanase producing capability has been reduced. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium isulphate, formic acid, and nucleotide analogues.

When such agents are used, the mutagenesis is typically performed by incubating the cell to be mutagenized in the presence of the mutagenizing agent of choice under suitable conditions, and selecting for cells exhibiting reduced Family 74 xyloglucanase activity or production.

Modification or inactivation of production of a polypeptide of the present invention may be accomplished by introduction, substitution, or removal of one or more nucleotides in the nucleic acid sequence encoding the polypeptide or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleic acid sequence to be modified, it is preferred that the modification be performed in vitro as exemplified below.

An example of a convenient way to eliminate or reduce production by a host cell of choice is by gene replacement or gene interruption. In the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. It may be desirable that the defective gene or gene fragment also encodes a marker which may be used for selection of transformants in which the gene encoding the polypeptide has been modified or destroyed.

Alternatively, modification or inactivation of the nucleic acid sequence may be performed by established anti-sense techniques using a nucleotide sequence complementary to the polypeptide encoding sequence. More specifically, production of the polypeptide by a cell may be reduced or eliminated by introducing a nucleotide sequence complementary to the nucleic-acid sequence encoding the polypeptide which may be transcribed in the cell and is capable of hybridizing to the polypeptide mRNA produced in the cell. Under conditions allowing the complementary anti-sense nucleotide sequence to hybridize to the polypeptide mRNA, the amount of polypeptide translated is thus reduced or eliminated.

It is preferred that the cell to be modified in accordance with the methods of the present invention is of microbial origin, for example, a fungal strain which is suitable for the production of desired protein products, either homologous or heterologous to the cell.

The present invention further relates to a mutant cell of a parent cell which comprises a disruption or deletion of a nucleic acid sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of Family 74 xyloglucanase activity by fermentation of a cell which produces both a polypeptide of the present invention as well as the protein product of interest by adding an effective amount of an agent capable of inhibiting Family 74 xyloglucanase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of Family 74 xyloglucanase activity by cultivating the cell under conditions permitting the expression of the product, subjecting the resultant culture broth to a combined pH and temperature treatment so as to reduce the Family 74 xyloglucanase activity substantially, and recovering the product from the culture broth. Alternatively, the combined pH and temperature treatment may be performed on an enzyme preparation recovered from the culture broth. The combined pH and temperature treatment may optionally be used in combination with a treatment with a xyloglucanase inhibitor.

In accordance with this aspect of the invention, it is possible to remove at least 60%, preferably at least 75%, more preferably at least 85%, still more preferably at least 95%, and most preferably at least 99% of the Family 74 xyloglucanase activity. Complete removal of xyloglucanase activity may be obtained by use of this method.

The combined pH and temperature treatment is preferably carried out at a pH in the range of 5–7 and a temperature in the range of 60–70° C. for a sufficient period of time to attain the desired effect, where typically, 30 to 60 minutes is sufficient.

The methods used for cultivation and purification of the product of interest may be performed by methods known in the art.

The methods of the present invention for producing an essentially xyloglucanase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellobiohydrolase, cellulase, chitinase, cutinase, cyclodextrin glycosyltransferase, deoxyribonuclease, endoglucanase, esterase, galactosidase, beta-galactosidase, glucoamylase, glucose oxidase, glucosidase (alpha or beta), haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The xyloglucanase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from Family 74 xyloglucanase activity which is produced by a method of the present invention.

Compositions

In a still further aspect, the present invention relates to compositions comprising a polypeptide of the present invention. Preferably, the compositions are enriched in a polypeptide of the present invention. In the present context, the term "enriched" indicates that the Family 74 xyloglucanase activity of the composition has been increased, e.g., with an enrichment factor of 1.1.

The composition may comprise a polypeptide of the invention as the major enzymatic component, e.g., a monocomponent composition. Alternatively, the composition may comprise multiple enzymatic activities, such as an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be producible by means of a microorganism belonging to the genus *Aspergillus*, preferably *Aspergillus aculeatus, Aspergillus awamori, Aspergillus niger*, or *Aspergillus oryzae*, or *Trichoderma, Humicola*, preferably *Humicola insolens*, or *Fusarium*, preferably *Fusarium bactridioides, Fusarium cerealis, Fusarium crookwellense, Fusarium culmorum, Fusarium graminearum, Fusarium graminum, Fusarium heterosporum, Fusarium negundi,* *Fusarium oxysporum, Fusarium reticulatum, Fusarium roseum, Fusarium sambucinum, Fusarium sarcochroum, Fusarium sulphureum, Fusarium toruloseum, Fusarium trichothecioides*, or *Fusarium venenatum*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Degradation of Biomass to Ethanol

The polypeptides of the present invention may be used in the production of ethanol from biomass. Ethanol can be produced by enzymatic degradation of biomass and conversion of the released polysaccharides to ethanol. This kind of ethanol is often referred to as bioethanol or biofuel. It can be used as a fuel additive or extender in blends of from less than 1% and up to 100% (a fuel substitute).

Biomass can include, but is not limited to, wood resources, municipal solid waste, wastepaper, and crop residues (see, for example, Wiselogel et al., 1995, in *Handbook on Bioethanol* (Charles E. Wyman, editor), pp. 105–118, Taylor & Francis, Washington D.C.; Wyman, 1994, *Bioresource Technology* 50: 3–16; Lynd, 1990, *Applied Biochemistry and Biotechnology* 24/25: 695–719; Mosier et al., 1999, *Recent Progress in Bioconversion of Lignocellulosics*, in *Advances in Biochemical Engineering/Biotechnology*, T. Scheper, managing editor, Volume 65, pp. 23–40, Springer-Verlag, New York,).

The predominant polysaccharide in the primary cell wall of biomass is cellulose, the second most abundant is hemicellulose, and the third is pectin. The secondary cell wall, produced after the cell has stopped growing, also contains polysaccharides and is strengthened through polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which helps stabilize the cell wall matrix.

Three major classes of cellulase enzymes are used to breakdown biomass:

(1) The "endo-1,4-beta-glucanases" or 1,4-beta-D-glucan-4-glucanohydrolases (EC 3.2.1.4), which act randomly on soluble and insoluble 1,4-beta-glucan substrates.

(2) The "exo-1,4-beta-D-glucanases" including both the 1,4-beta-D-glucan glucohydrolases (EC 3.2.1.74), which liberate D-glucose from 1,4-beta-D-glucans and hydrolyze D-cellobiose slowly, and 1,4-beta-D-glucan cellobiohydrolase (EC 3.2.1.91), also referred to as cellobiohydrolase 1, which liberates D-cellobiose from 1,4-beta-glucans.

(3) The "beta-D-glucosidases" or beta-D-glucoside glucohydrolases (EC 3.2.1.21), which act to release D-glucose units from cellobiose and soluble cellodextrins, as well as an array of glycosides.

These three classes of enzymes work together synergistically in a complex interplay that results in efficient decrystallization and hydrolysis of native cellulose from biomass to yield the reducing sugars which are converted to ethanol by fermentation.

The polypeptides of the present invention may be used in conjunction with the above-noted enzymes to further degrade the hemicellulose component of the biomass substrate, (see, for example, Brigham et al., 1995, in *Handbook on Bioethanol* (Charles E. Wyman, editor), pp. 119–141, Taylor & Francis, Washington D.C.; Lee, 1997, *Journal of Biotechnology* 56: 1–24).

The polypeptides of the present invention may be used as a component in detergents.

Use in the Detergent Industry

During washing and wearing, dyestuff from dyed fabrics or garment will conventionally bleed from the fabric, which then looks faded and worn. Removal of surface fibers from the fabric will partly restore the original colors and looks of the fabric. By the term "color clarification", as used herein, is meant the partly restoration of the initial colors of fabric or garment throughout multiple washing cycles.

The term "de-pilling" denotes removing of pills from the fabric surface.

The term "soaking liquor" denotes aqueous liquor in which laundry may be immersed prior to being subjected to a conventional washing process. The soaking liquor may contain one or more ingredients conventionally used in a washing or laundering process.

The term "washing liquor" denotes aqueous liquor in which laundry is subjected to a washing process, i.e., usually a combined chemical and mechanical action either manually or in a washing machine. Conventionally, the washing liquor is an aqueous solution of a powder or liquid detergent composition.

The term "rinsing liquor" denotes aqueous liquor in which laundry is immersed and treated, conventionally immediately after being subjected to a washing process, in order to rinse the laundry, i.e., essentially remove the detergent solution from the laundry. The rinsing liquor may contain a fabric conditioning or softening composition.

The laundry subjected to the method of the present invention may be conventional washable laundry. Preferably, the major part of the laundry is sewn or unsewn fabrics, including knits, wovens, denims, yarns, and toweling, made from cotton, cotton blends or natural or manmade cellulosics (e.g., originating from xylan-containing cellulose fibers such as from wood pulp) or blends thereof. Examples of blends are blends of cotton or rayon/viscose with one or more companion material such as wool, synthetic fibers (e.g., polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g., rayon/viscose, ramie, flax/linen, jute, cellulose acetate fibers, lyocell).

Surfactant system. The detergent compositions according to the present invention comprise a surfactant system, wherein the surfactant can be selected from non-ionic and/or anionic and/or cationic and/or ampholytic and/or zwitterionic and/or semi-polar surfactants. The surfactant is typically present at a level from 0.1% to 60% by weight. The surfactant is preferably formulated to be compatible with enzyme components present in the composition. In liquid or gel compositions the surfactant is most preferably formulated in such a way that it promotes, or at least does not degrade, the stability of any enzyme in these compositions.

Preferred systems to be used according to the present invention comprise as a surfactant one or more of the non-ionic and/or anionic surfactants described herein.

Polyethylene, polypropylene, and polybutylene oxide conden-sates of alkyl phenols are suitable for use as the non-ionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available non-ionic surfactants of this type include Igepal™ CO-630, marketed by the GAF Corporation; and Triton™ X-45, X-114, X-100 and X-102, all marketed by the Rohm & Haas Company. These surfactants are commonly referred to as alkyl phenol alkoxylates (e.g., alkyl phenol ethoxylates).

The condensation products of primary and secondary aliphatic alcohols with about 1 to about 25 moles of ethylene oxide are suitable for use as the non-ionic surfactant of the non-ionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available non-ionic surfactants of this type include Tergitol™ 15-S-9 (The condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA 050 (the condensation product of $C_{12}$–$C_{14}$ alcohol with 5 moles of ethylene oxide) marketed by Hoechst. Preferred range of HLB in these products is from 8–11 and most preferred from 8–10.

Also useful as the non-ionic surfactant of the surfactant systems of the present invention are alkyl polysaccharides disclosed in U.S. Pat. No. 4,565,647, having a hydrophobic group containing from about 6 to about 30 carbon atoms, preferably from about 10 to about 16 carbon atoms and a polysaccharide, e.g., a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6-positions on the preceding saccharide units.

The preferred alkyl polyglycosides have the formula

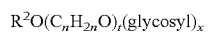

wherein $R^2$ is selected from the group consisting of alkyl, alkyl phenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4-, and/or 6-position, preferably predominantly the 2-position.

The condensation products of ethylene oxide with a hydrophobic base formed by the condensation of propylene oxide with propylene glycol are also suitable for use as the additional non-ionic surfactant systems of the present invention. The hydrophobic portion of these compounds will preferably have a molecular weight from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic™ surfactants, marketed by BASF.

Also suitable for use as the non-ionic surfactant of the non-ionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of non-ionic surfactant include certain of the commercially available Tetronic™ compounds, marketed by BASF.

Preferred for use as the non-ionic surfactant of the surfactant systems of the present invention are polyethylene oxide condensates of alkyl phenols, condensation products of primary and secondary aliphatic alcohols with from about 1 to about 25 moles of ethylene oxide, alkyl polysaccharides, and mixtures hereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof. Highly preferred non-ionic surfactants are polyhydroxy fatty acid amide surfactants of the formula

wherein $R^1$ is H, or $R^1$ is $C_{1-4}$ hydrocarbyl, 2-hydroxyethyl, 2-hydroxypropyl or a mixture thereof, $R^2$ is $C_{5-31}$ hydrocarbyl, and Z is a polyhydroxy hydrocarbyl having a linear hydrocarbyl chain with at least 3 hydroxyls directly connected to the chain, or an alkoxylated derivative thereof. Preferably, $R^1$ is methyl, $R^2$ is straight $C_{11-15}$ alkyl or $C_{16-18}$ alkyl or alkenyl chain such as coconut alkyl or mixtures thereof, and Z is derived from a reducing sugar such as glucose, fructose, maltose or lactose, in a reductive amination reaction.

Highly preferred anionic surfactants include alkyl alkoxylated sulfate surfactants. Examples hereof are water soluble salts or acids of the formula $RO(A)_mSO3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethyl-ammonium cations and quaternary ammonium cations such as tetramethyl-ammonium and dimethyl piperdinium cations and those derived from alkylamines such as ethylamine, diethyl amine, triethylamine, mixtures thereof, and the like. Exemplary surfactants are $C_{12}$–$C_{18}$ alkyl polyethoxylate (1.0) sulfate ($C_{12}$–$C_{18}$E(1.0)M), $C_{12}$–$C_{18}$ alkyl polyethoxylate (2.25) sulfate ($C_{12}$–$C_{18}$(2.25)M, and $C_{12}$–$C_{18}$ alkyl polyethoxylate (3.0) sulfate ($C_{12}$–$C_{18}$E(3.0)M), and $C_{12}$–$C_{18}$ alkyl polyethoxylate (4.0) sulfate ($C_{12}$–$C_{18}$E(4.0)M), wherein M is conveniently selected from sodium and potassium.

Suitable anionic surfactants to be used are alkyl ester sulfonate surfactants including linear esters of $C_8$–$C_{20}$ carboxylic acids (i.e., fatty acids), which are, sulfonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

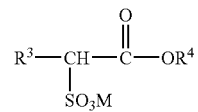

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation, which forms a water-soluble salt with the alkyl ester sulfonate. Suitable salt-forming cations include metals such as sodium, potassium, and lithium, and substituted or unsubstituted ammonium cations, such as monoethanolamine, diethanolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants which are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g., below about 50° C.) and $C_{16}$–$C_{18}$ alkyl chains are preferred for higher wash temperatures (e.g., above about 50° C.).

Other anionic surfactants useful for detersive purposes can also be included in the laundry detergent compositions of the present invention. These can include salts (including, for example, sodium, potassium, ammonium, and substituted ammonium salts such as mono-di- and triethanolamine salts) of soap, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula $RO(CH_2CH_2O)_k$—$CH_2COO$—M+ wherein R is a $C_8$–$C_{22}$ alkyl, k is an integer from 1 to 10, and M is a soluble salt forming cation. Resin acids and hydrogenated resin acids are also suitable, such as rosin, hydrogenated rosin, and resin acids and hydrogenated resin acids present in or derived from tall oil.

Alkylbenzene sulfonates are highly preferred. Especially preferred are linear (straight-chain) alkyl benzene sulfonates (LAS) wherein the alkyl group preferably contains from 10 to 18 carbon atoms.

Further examples are described in "Surface Active Agents and Detergents" (Vol. I and II by Schwartz, Perrry and Berch). A variety of such surfactants are also generally disclosed in U.S. Pat. No. 3,929,678, (Column 23, line 58 through Column 29, line 23, herein incorporated by reference).

When included therein, the laundry detergent compositions of the present invention typically comprise from about 1% to about 40%, preferably from about 3% to about 20% by weight of such anionic surfactants.

The laundry detergent compositions of the present invention may also contain cationic, ampholytic, zwitterionic, and semi-polar surfactants, as well as the nonionic and/or anionic surfactants other than those already described herein.

Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

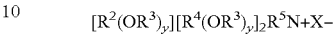

wherein $R^2$ is an alkyl or alkyl benzyl group having from about 8 to about 18 carbon atoms in the alkyl chain, each $R^3$ is selected form the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl ring structures formed by joining the two $R^4$ groups, —$CH_2CHOHCHOHCOR^6CHOHCH_2OH$, wherein $R^6$ is any hexose or hexose polymer having a molecular weight less than about 1000, and hydrogen when y is not 0; $R^5$ is the same as $R^4$ or is an alkyl chain, wherein the total number of carbon atoms or $R^2$ plus $R^5$ is not more than about 18; each y is from 0 to about 10, and the sum of the y values is from 0 to about 15; and X is any compatible anion.

Highly preferred cationic surfactants are the water-soluble quaternary ammonium compounds useful in the present composition having the formula:

$$R_1R_2R_3R_4N^+X^- \qquad (i)$$

wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and —$(C_2H_{4O})_xH$ where x has a value from 2 to 5, and X is an anion. Not more than one of $R_2$, $R_3$ or $R_4$ should be benzyl.

The preferred alkyl chain length for $R_1$ is $C_{12}$–$C_{15}$, particularly where the alkyl group is a mixture of chain lengths derived from coconut or palm kernel fat or is derived synthetically by olefin build up or OXO alcohols synthesis.

Preferred groups for $R_2R_3$ and $R_4$ are methyl and hydroxyethyl groups and the anion X may be selected from halide, methosulphate, acetate and phosphate ions.

Examples of suitable quaternary ammonium compounds of formulae (i) for use herein are:
coconut trimethyl ammonium chloride or bromide;
coconut methyl dihydroxyethyl ammonium chloride or bromide;
decyl triethyl ammonium chloride;
decyl dimethyl hydroxyethyl ammonium chloride or bromide;
$C_{12-15}$ dimethyl hydroxyethyl ammonium chloride or bromide;
coconut dimethyl hydroxyethyl ammonium chloride or bromide;
myristyl trimethyl ammonium methyl sulphate;
lauryl dimethyl benzyl ammonium chloride or bromide;
lauryl dimethyl (ethenoxy)$_4$ ammonium chloride or bromide;
choline esters (compounds of formula (i) wherein $R_1$ is

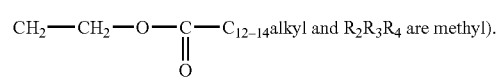

di-alkyl imidazolines [compounds of formula (i)].
Other cationic surfactants useful herein are also described in U.S. Pat. No. 4,228,044 and in EP 000 224.

When included therein, the laundry detergent compositions of the present invention typically comprise from 0.2% to about 25%, preferably from about 1% to about 8% by weight of such cationic surfactants.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g., carboxy, sulfonate, sulfate. See U.S. Pat. No. 3,929,678 (column 19, lines 18–35) for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 (column 19, line 38 through column 22, line 48) for examples of zwitterionic surfactants.

When included therein, the laundry detergent compositions of the present invention typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula:

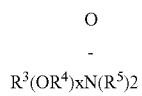

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3: and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

When included therein, the laundry detergent compositions of the present invention typically comprise from 0.2% to about 15%, preferably from about 1% to about 10% by weight of such semi-polar nonionic surfactants.

Builder system. The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g., SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenleenschrift 2,446,686, and 2,446,487, U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2,-ethane tetracarboxylates, 1,1,3,3-propane tetrac7arboxylates containing sulfo substituents include the sulfosuccinate derivatives disclosed in British Patent Nos. 1,398,421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis-cis-tetracarboxylates, cyclopentadienide pentacarboxylates, 2,3,4,5-tetrahydro-furan-cis,cis,cis-tetracarboxylates, 2,5-tetrahydro-furan-cis, discarboxylates, 2,2,5,5,-tetrahydrofuran-tetracarboxylates, 1,2,3,4,5,6-hexane-hexacarboxylates and carboxymethyl derivatives of polyhydric alcohols such as sorbitol, mannitol and xylitol. Aromatic polycarboxylates include mellitic acid, pyromellitic acid and the phthalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelant for inclusion in the detergent compositions in accordance with the invention is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include $Na_2EDDS$ and $Na_4EDDS$. Examples of such preferred magnesium salts of EDDS include MgEDDS and $Mg_2EDDS$. The magnesium salts are the most preferred for inclusion in compositions in accordance with the invention.

Preferred builder systems include a mixture of a water-insoluble aluminosilicate builder such as zeolite A, and a water soluble carboxylate chelating agent such as citric acid.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated form each other by not more than two carbon atoms.

Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 5% to 80% by weight of the composition. Preferred levels of builder for liquid detergents are from 5% to 30%.

Enzymes. Preferred detergent compositions, in addition to the enzyme preparation of the invention, comprise other enzyme(s) which provides cleaning performance and/or fabric care benefits. Such enzymes include proteases, lipases, cutinases, amylases, cellulases, peroxidases, oxidases (e.g., laccases).

Proteases: Any protease suitable for use in alkaline solutions can be used. Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270.

Preferred commercially available protease enzymes include those sold under the trade names Alcalase, Savinase, Primase, Durazym, and Esperase by Novozymes A/S, those sold under the tradename Maxatase, Maxacal, Maxapem, Properase, Purafect and Purafect OXP by Genencor International, and those sold under the tradename Opticlean and Optimase by Solvay Enzymes. Protease enzymes may be incorporated into the compositions in accordance with the invention at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Lipases: Any lipase suitable for use in alkaline solutions can be used. Suitable lipases include those of bacterial or fungal origin. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238 023, a *Candida lipase*, such as a *C. antarctica* lipase, e.g., the *C. antarctica* lipase A or B described in EP 214 761, a *Pseudomonas* lipase such as a *P. alcaligenes* and *P. pseudoalcaligenes* lipase, e.g., as described in EP 218 272, a *P. cepacia* lipase, e.g., as described in EP 331 376, a *P. stutzeri* lipase, e.g., as disclosed in GB 1,372,034, a *P. fluorescens* lipase, a *Bacillus* lipase, e.g., a *B. subtilis* lipase (Dartois et al., (1993), BBA 1131, 253–260), a *B. stearothermophilus* lipase (JP 64/744992), and a *B. pumilus* lipase (WO 91/16422).

Furthermore, a number of cloned lipases may be useful, including the *Penicillium camembertii* lipase described by Yamaguchi et al., (1991), *Gene* 103, 61–67), the *Geotricum candidum* lipase (Schimada, Y. et al., (1989), *J. Biochem.*, 106, 383–388), and various *Rhizopus* lipases such as a *R. delemar* lipase (Hass et al., (1991), *Gene* 109, 117–113), a *R. niveus* lipase (Kugimiya et al., (1992), *Biosci. Biotech. Biochem.* 56, 716–719) and a *R. oryzae* lipase.

Other types of lipolytic enzymes such as cutinases may also be useful, e.g., a cutinase derived from *Pseudomonas mendocina* as described in WO 88/09367, or a cutinase derived from *Fusarium solanipisi* (e.g., described in WO 90/09446).

Especially suitable lipases are lipases such as M1 Lipase™, Luma fast™ and Lipomax™ (Genencor), Lipolase™ and Lipolase Ultra™ (Novozymes A/S), and Lipase P "Amano" (Amano Pharmaceutical Co. Ltd.).

The lipases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Amylases: Any amylase (a and/or b) suitable for use in alkaline solutions can be used. Suitable amylases include those of bacterial or fungal origin. Chemically or genetically modified mutants are included. Amylases include, for example, alpha-amylases obtained from a special strain of *B. licheniformis*, described in more detail in GB 1,296,839. Commercially available amylases are Duramyl™, Termamyl™, Fungamyl™ and BAN™ (Novozymes A/S) and Rapidase™ and Maxamyl P™ (Genencor).

The amylases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, and even more preferably at a level of from 0.01% to 0.2% of enzyme protein by weight of the composition.

Cellulases: Any cellulase suitable for use in alkaline solutions can be used. Suitable cellulases include those of bacterial or fungal origin. Chemically or genetically modified mutants are included. Suitable cellulases are disclosed in U.S. Pat. No. 4,435,307 which discloses fungal cellulases produced from *Humicola insolens*, in WO 96/34108 and WO 96/34092 which disclose bacterial alkalophilic cellulases (BCE 103) from *Bacillus*, and in WO 94/21801, U.S. Pat. No. 5,475,101 and U.S. Pat. No. 5,419,778 which disclose EG III cellulases from *Trichoderma*. Especially suitable cellulases are the cellulases having colour care benefits. Examples of such cellulases are cellulases described in European patent application No. 0 495 257. Commercially available cellulases include Celluzyme™ and Carezyme™ produced by a strain of *Humicola insolens* (Novozymes A/S), KAC-500(B)™ (Kao Corporation), and Puradax™ (Genencor International).

Cellulases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Peroxidases/Oxidases: Peroxidase enzymes are used in combination with hydrogen peroxide or a source thereof (e.g., a percarbonate, perborate or persulfate). Oxidase enzymes are used in combination with oxygen. Both types of enzymes are used for "solution bleaching", i.e., to prevent transfer of a textile dye from a dyed fabric to another fabric when said fabrics are washed together in a wash liquor, preferably together with an enhancing agent as described in e.g., WO 94/12621 and WO 95/01426. Suitable peroxidases/oxidases include those of plant, bacterial or fungal origin. Chemically or genetically modified mutants are included.

Peroxidase and/or oxidase enzymes are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, and even more preferably at a level of from 0.01% to 0.2% of enzyme protein by weight of the composition.

Mixtures of the above mentioned enzymes are encompassed herein, in particular a mixture of a protease, an amylase, a lipase and/or a cellulase.

The enzyme of the invention, or any other enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, and even more preferably at a level from 0.01% to 0.2% of enzyme protein by weight of the composition.

Bleaching agents. Additional optional detergent ingredients that can be included in the detergent compositions of the present invention include bleaching agents such as PB1, PB4 and percarbonate with a particle size of 400–800 microns. These bleaching agent components can include one or more oxygen bleaching agents and, depending upon the bleaching agent chosen, one or more bleach activators. When present oxygen bleaching compounds will typically be present at levels of from about 1% to about 25%. In general, bleaching compounds are optional added components in non-liquid formulations, e.g., granular detergents.

The bleaching agent component for use herein can be any of the bleaching agents useful for detergent compositions including oxygen bleaches as well as others known in the art. The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483,781, U.S. Pat. No. 740,446, EP 0 133 354 and U.S. Pat. No. 4,412,934. Highly preferred bleaching agents also include 6-nonylamino-6-oxoperoxycaproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetra-acetylethylenediamine (TAED), nonanoyloxybenzenesulfonate (NOBS, described in U.S. Pat. No. 4,412,934), 3,5-trimethyl-hexsanoloxybenzenesulfonate (ISONOBS, described in EP 120 591) or pentaacetylglucose (PAG), which are perhydrolyzed to form a peracid as the active bleaching species, leading to improved bleaching effect. In addition, very suitable are the bleach activators C8(6-octanamidocaproyl) oxybenzene-sulfonate, C9(6-nonanamido caproyl) oxybenzenesulfonate and C10 (6-decanamido caproyl) oxybenzenesulfonate or mixtures thereof. Also suitable activators are acylated citrate esters such as disclosed in European Patent Application No. 91870207.7.

Useful bleaching agents, including peroxyacids and bleaching systems comprising bleach activators and peroxygen bleaching compounds for use in cleaning compositions according to the invention are described in application U.S. Ser. No. 08/136,626.

The hydrogen peroxide may also be present by adding an enzymatic system (i.e., an enzyme and a substrate therefore) which is capable of generation of hydrogen peroxide at the beginning or during the washing and/or rinsing process. Such enzymatic systems are disclosed in European Patent Application EP 0 537 381.

Bleaching agents other than oxygen bleaching agents are also known in the art and can be utilized herein. One type of non-oxygen bleaching agent of particular interest includes photoactivated bleaching agents such as the sulfonated zinc and/or aluminum phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent composition will contain about 0.025% to about 1.25%, by weight, of sulfonated zinc phthalocyanine.

Bleaching agents may also comprise a manganese catalyst. The manganese catalyst may, e.g., be one of the compounds described in "Efficient manganese catalysts for low-temperature bleaching", *Nature* 369, 1994, pp. 637–639.

Suds suppressors. Another optional ingredient is a suds suppressor, exemplified by silicones, and silica-silicone mixtures. Silicones can generally be represented by alkylated polysiloxane materials, while silica is normally used in finely divided forms exemplified by silica aerogels and xerogels and hydrophobic silicas of various types. Theses materials can be incorporated as particulates, in which the suds suppressor is advantageously releasably incorporated in a water-soluble or waterdispersible, substantially non surface-active detergent impermeable carrier. Alternatively the suds suppressor can be dissolved or dispersed in a liquid carrier and applied by spraying on to one or more of the other components.

A preferred silicone suds controlling agent is disclosed in U.S. Pat. No. 3,933,672. Other particularly useful suds suppressors are the self-emulsifying silicone suds suppressors, described in German Patent Application DTOS 2,646, 126. An example of such a compound is DC-544, commercially available form Dow Corning, which is a siloxane-glycol copolymer. Especially preferred suds controlling agent are the suds suppressor system comprising a mixture of silicone oils and 2-alkyl-alkanols. Suitable 2-alkyl-alkanols are 2-butyl-octanol which are commercially available under the trade name Isofol 12 R.

Such suds suppressor system are described in European Patent Application EP 0 593 841.

Especially preferred silicone suds controlling agents are described in European Patent Application No. 92201649.8. The compositions can comprise a silicone/silica mixture in combination with fumed nonporous silica such as Aerosil®.

The suds suppressors described above are normally employed at levels of from 0.001% to 2% by weight of the composition, preferably from 0.01% to 1% by weight.

Other components. Other components used in detergent compositions may be employed such as soil-suspending agents, soil-releasing agents, optical brighteners, abrasives, bactericides, tarnish inhibitors, coloring agents, and/or encapsulated or nonencapsulated perfumes.

Especially suitable encapsulating materials are water-soluble capsules which consist of a matrix of polysaccharide and polyhydroxy compounds such as described in GB 1,464,616.

Other suitable water soluble encapsulating materials comprise dextrins derived from ungelatinized starch acid esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulation materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably form 0.75% to 8%, most preferably from 1% to 6% by weight of the composition.

Preferred optical brighteners are anionic in character, examples of which are disodium 4,4'-bis-(2-diethanolamino-4-anilino-s-triazin-6-ylamino)stilbene-2:2'-disulphonate, disodium 4,-4'-bis-(2-morpholino-4-anilino-s-triazin-6-ylamino-stilbene-2:2'-disulphonate, disodium 4,4'-bis-(2,4-dianilino-s-triazin-6-ylamino)stilbene-2:2'-disulphonate, monosodium 4',4"-bis-(2,4-dianilino-s-tri-azin-6-ylamino) stilbene-2-sulphonate, disodium 4,4'-bis-(2-anilino-4-(N-methyl-N-2-hydroxyethylamino)-s-triazin-6-ylamino)stilbene-2,2'-disulphonate, di-sodium 4,4'-bis-(4-phenyl-2,1,3-triazol-2-yl)-stilbene-2,2' disulphonate, di-sodium 4,4'-bis (2-anilino-4-(1-methyl-2-hydroxyethylamino)-s-triazin-6-ylami-no)stilbene-2,2'-disulphonate, sodium 2(stilbyl-4"-(naphtho-1',2':4,5)-1,2,3,-triazole-2"-sulphonate and 4,4'-bis (2-sulphostyryl)biphenyl.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in U.S. Pat. Nos. 4,116,885 and 4,711,730 and EP 0 272 033. A particular preferred polymer in accordance with EP 0 272 033 has the formula:

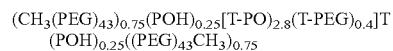

$(POH)_{0.25}((PEG)_{43}CH_3)_{0.75}$ wherein PEG is —$(OC_2H_4)O$—, PO is $(OC_3H_6O)$ and T is $(pOOC_6H_4CO)$.

Also very useful are modified polyesters as random copolymers of dimethyl terephthalate, dimethyl sulfoisophthalate, ethylene glycol and 1,2-propanediol, the end groups consisting primarily of sulphobenzoate and secondarily of mono esters of ethylene glycol and/or 1,2-propanediol. The target is to obtain a polymer capped at both end by sulphobenzoate groups, "primarily", in the present context most of said copolymers herein will be endcapped by sulphobenzoate groups. However, some copolymers will be less than fully capped, and therefore their end groups may consist of monoester of ethylene glycol and/or 1,2-propanediol, thereof consist "secondarily" of such species.

The selected polyesters herein contain about 46% by weight of dimethyl terephthalic acid, about 16% by weight of 1,2-propanediol, about 10% by weight ethylene glycol, about 13% by weight of dimethyl sulfobenzoic acid and about 15% by weight of sulfoisophthalic acid, and have a molecular weight of about 3.000. The polyesters and their method of preparation are described in detail in EP 311 342.

Softening agents. Fabric softening agents can also be incorporated into laundry detergent compositions in accordance with the present invention. These agents may be inorganic or organic in type. Inorganic softening agents are exemplified by the smectite clays disclosed in GB-A-1 400898 and in U.S. Pat. No. 5,019,292. Organic fabric softening agents include the water insoluble tertiary amines as disclosed in GB-A1 514 276 and EP 0 011 340 and their combination with mono $C_{12}$–$C_{14}$ quaternary ammonium salts are disclosed in EP-B-0 026 528 and di-long-chain amides as disclosed in EP 0 242 919. Other useful organic ingredients of fabric softening systems include high molecular weight polyethylene oxide materials as disclosed in EP 0 299 575 and 0 313 146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or di-chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Polymeric dye-transfer inhibiting agents. The detergent compositions according to the present invention may also comprise from 0.001% to 10%, preferably from 0.01% to 2%, more preferably form 0.05% to 1% by weight of polymeric dye-transfer inhibiting agents. Said polymeric dye-transfer inhibiting agents are normally incorporated into detergent compositions in order to inhibit the transfer of dyes from colored fabrics onto fabrics washed therewith. These polymers have the ability of complexing or adsorbing the fugitive dyes washed out of dyed fabrics before the dyes have the opportunity to become attached to other articles in the wash.

Especially suitable polymeric dye-transfer inhibiting agents are polyamine N-oxide polymers, copolymers of N-vinyl-pyrrolidone and N-vinylimidazole, polyvinylpyrrolidone polymers, polyvinyloxazolidones and polyvinylimidazoles or mixtures thereof. Addition of such polymers also enhances the performance of the enzymes according the invention.

The detergent composition according to the invention can be in liquid, paste, gels, bars or granular forms.

Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Granular compositions according to the present invention can also be in "compact form", i.e., they may have a relatively higher density than conventional granular detergents, i.e. form 550 to 950 g/l; in such case, the granular detergent compositions according to the present invention will contain a lower amount of "inorganic filler salt", compared to conventional granular detergents; typical filler salts are alkaline earth metal salts of sulphates and chlorides, typically sodium sulphate; "Compact" detergent typically comprise not more than 10% filler salt. The liquid compositions according to the present invention can also be in "concentrated form", in such case, the liquid detergent compositions according to the present invention will contain a lower amount of water, compared to conventional liquid detergents. Typically, the water content of the concentrated liquid detergent is less than 30%, more preferably less than 20%, and most preferably less than 10% by weight of the detergent compositions.

The compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The following examples are meant to exemplify compositions for the present invention, but are not necessarily meant to limit or otherwise define the scope of the invention. In the detergent compositions, the abbreviated component identifications have the following meanings:

| | |
|---|---|
| LAS: | Sodium linear $C_{12}$ alkyl benzene sulphonate |
| TAS: | Sodium tallow alkyl sulphate |
| XYAS: | Sodium $C_{1X}$–$C_{1Y}$ alkyl sulfate |
| SS: | Secondary soap surfactant of formula 2-butyl octanoic acid |
| 25EY: | A $C_{12}$–$C_{15}$ predominantly linear primary alcohol condensed with an average of Y moles of ethylene oxide |
| 45EY: | A $C_{14}$–$C_{15}$ predominantly linear primary alcohol condensed with an average of Y moles of ethylene oxide |
| XYEZS: | $C_{1X}$–$C_{1Y}$ sodium alkyl sulfate condensed with an average of Z moles of ethylene oxide per mole |
| Nonionic: | $C_{13}$–$C_{15}$ mixed ethoxylated/propoxylated fatty alcohol with an average degree of ethoxylation of 3.8 and an average degree of propoxylation of 4.5 sold under the tradename Plurafax LF404 by BASF Gmbh |
| CFAA: | $C_{12}$–$C_{14}$ alkyl N-methyl glucamide |
| TFAA: | $C_{16}$–$C_{18}$ alkyl N-methyl glucamide |
| Silicate: | Amorphous Sodium Silicate ($SiO_2$:$Na_2O$ ratio = 2.0) |
| NaSKS-6: | Crystalline layered silicate of formula d-$Na_2Si_2O_5$ |
| Carbonate: | Anhydrous sodium carbonate |
| Phosphate: | Sodium tripolyphosphate |
| MA/AA: | Copolymer of 1:4 maleic/acrylic acid, average molecular weight about 80,000 |
| Polyacrylate: | Polyacrylate homopolymer with an average molecular weight of 8,000 sold under the tradename PA30 by BASF GmbH |
| Zeolite A: | Hydrated Sodium Aluminosilicate of formula $Na_{12}(AlO_2SiO_2)_{12}.27H_2O$ having a primary particle size in the range from 1 to 10 micrometers |
| Citrate: | Tri-sodium citrate dihydrate |
| Citric: | Citric Acid |
| Perborate: | Anhydrous sodium perborate monohydrate bleach, empirical formula $NaBO_2.H_2O_2$ |
| PB4: | Anhydrous sodium perborate tetrahydrate |
| Percarbonate: | Anhydrous sodium percarbonate bleach of empirical formula $2Na_2CO_3.3H_2O_2$ |
| TAED: | Tetraacetyl ethylene diamine |
| CMC: | Sodium carboxymethyl cellulose |
| DETPMP: | Diethylene triamine penta (methylene phosphonic acid), marketed by Monsanto under the Tradename Dequest 2060 |
| PVP: | Polyvinylpyrrolidone polymer |
| EDDS: | Ethylenediamine-N,N'-disuccinic acid, [S,S] isomer in the form of the sodium salt |
| Suds Suppressor: | 25% paraffin wax Mpt 50° C., 17% hydrophobic silica, 58% paraffin oil |
| Granular Suds suppressor: | 12% Silicone/silica, 18% stearyl alcohol, 70% starch in granular form |
| Sulphate: | Anhydrous sodium sulphate |
| HMWPEO: | High molecular weight polyethylene oxide |
| TAE 25: | Tallow alcohol ethoxylate (25) |

DETERGENT EXAMPLE I

A granular fabric cleaning composition in accordance with the invention may be prepared as follows:

| | |
|---|---|
| Sodium linear $C_{12}$ alkyl benzene sulfonate | 6.5 |
| Sodium sulfate | 15.0 |
| Zeolite A | 26.0 |
| Sodium nitrilotriacetate | 5.0 |

-continued

| | |
|---|---|
| Enzyme of the invention | 0.1 |
| PVP | 0.5 |
| TAED | 3.0 |
| Boric acid | 4.0 |
| Perborate | 18.0 |
| Phenol sulphonate | 0.1 |
| Minors | Up to 100 |

DETERGENT EXAMPLE II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme of the invention | 0.1 |
| TAED | 6.0 |
| Percarbonate | 22.0 |
| EDDS | 0.3 |
| Granular suds suppressor | 3.5 |
| water/minors | Up to 100% |

DETERGENT EXAMPLE III

Granular fabric cleaning compositions in accordance with the invention which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme of the invention | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinyl-imidazole and vinyl-pyrrolidone | — | 0.2 |
| Perborate | 1.0 | — |
| Phenol sulfonate | 0.2 | — |
| Water/Minors | Up to 100% | |

DETERGENT EXAMPLE IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme of the invention | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

DETERGENT EXAMPLE V

Heavy duty liquid fabric cleaning compositions in accordance with the invention may be prepared as follows:

| | I | II |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme of the invention | 0.10 | 0.05 |
| Coco-alkyl dimethyl hydroxy ethyl ammonium chloride | — | 3.0 |
| Smectite clay | — | 5.0 |
| PVP | 2.0 | — |
| Water/Minors | Up to 100% | |

Wash Evaluation of Xyloglucanases. The following provides general guidelines on how to perform a wash evaluation of detergent compositions containing xyloglucanases.

Preparation of tamarind gum swatches 5 liter of ionized water is heated to 50° C. and then 10 g of Tamarind seed polysaccharide is added slowly during agitation. The suspension is agitated until the polymer is solubilized. Clean cotton swatches (style 400 from Testfabrics Inc.) are placed in the solution for 30 min, squeezed between two rolls and dried overnight. The swatches are rinsed an EU wash machine, dried overnight and cut into 5 cm×5 cm pieces.

Preparation of dinginess swatches: Old white cotton fabrics are cut into 5 cm×5 cm pieces.

Wash in Launder-o-meter. Each beaker (500 ml) is added steel balls, 200 ml detergent solution and 6–12 dinginess or tamarind gum swatches. The wash cycle is conducted and the swatches are rinsed in tap water and air dried overnight at room temperature.

Iron oxide soiling. The following mixture is prepared and stirred for 30 minutes:

5,25 g $Fe_2O_3$ (Merck 3924)
800 ml ionised water
42 ml $Na_2CO_3$ (5 g/l)

The swatches and iron oxide solution is placed in a Japanese washing machine (NA-F38A1M) using the programme "Large SPEEDY" (42 l of water, 3 minute wash, 1 rinse, 3 minute centrifuging). The swatches are air dried overnight at room temperature.

Evaluation. Remission of the swatches is measured at 440 nm using a MacBeth ColorEye 7000 remission spectrophotometer. The results are expressed as Delta remission= $R_{enzyme, \ after \ soiling} - R_{control, \ after \ soiling}$, where R is the remission at 440 nm.

Data. The effect on the tamarind gum swatches expresses the effect of the xyloglucanase during wash on tamarind gum containing stains e.g., food stains, whereas the effect on the dinginess swatches expresses the general cleaning effect of the xyloglucanase during wash.

Signal Peptide

The present invention also relates to nucleic acid constructs comprising a gene encoding a protein operably linked to one or both of a first nucleic acid sequence consisting of nucleotides 59 to 114 of SEQ ID NO: 1 encoding a signal peptide consisting of amino acids 1 to 19 of SEQ ID NO: 2, wherein the gene is foreign to the nucleic acid sequence.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The nucleic acid sequence may be operably linked to foreign genes with other control sequences. Such other control sequences are described supra. As noted earlier, where both signal peptide and propeptide regions are present at the amino terminus of a protein, the propeptide region is positioned next to the amino terminus of a protein and the signal peptide region is positioned next to the amino terminus of the propeptide region.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred embodiment, the protein is an oxidoreductase, transferase, hydrolase, lyase, isomerase, or ligase. In an even more preferred embodiment, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Chemicals used as buffers and substrates were commercial products of at least reagent grade.

Strains

*Trichoderma reesei* Tv10 is an isolate of *Trichoderma reesei* strain Rut C-30, ATCC 56765 (Wiebe et al., 1991, *Mycol. Research* 95: 1284–1288), *Trichoderma reesei* strain NRRL 6156.

Media and Solutions

AMG trace metals solution was composed per liter of 14.3 g of $ZnSO_4.7H_2O$, 2.5 g of $CuSO_4.5H_2O$, 0.5 g of $NiCl_2$, 13.8 g of $FeSO_4$, 8.5 g of $MnSO_4$, and 3.0 g of citric acid.

Biotin stock solution was composed of 5 mg of biotin in 100 ml of 50% ethanol.

50× Vogels medium was composed per liter of 150 g of sodium citrate, 250 g of $KH_2PO_4$, 10 g of $MgSO_4.7H_2O$, 10 g of $CaCl_2.2H_2O$, 2.5 ml of biotin stock solution, and 5.0 ml of 50× Vogels trace metals solution.

50× Vogels trace metals solution was composed per liter of 50 g of citric acid, 50 g of $ZnSO_4.7H_2O$, 10 g of $Fe(NH_4)_2(SO_4)_2.6H_2O$, 2.5 g of $CuSO_4.5H_2O$, 0.5 g of $MnSO_4$, 0.5 g of $H_3BO_3$, and 0.5 g of $Na_2MoO_4.2H_2O$.

50× Vogels $NO_3$ stock was composed per liter of 125 g of sodium citrate, 250 g of $KH_2PO_4$, 106.25 g of $NaNO_3$, 10 g of $MgSO_4.7H_2O$, 5 g of $CaCl_2.2H_2O$, 2.5 ml of biotin stock solution, and 5.0 ml of 50× Vogels trace metals solution.

50× Vogels $NO_3$ plus BASTA (5 mg/ml) medium was composed per liter of 20 ml 50× Vogels, 24 mM $NaNO_3$, 25 g of sucrose, 25 g of Noble agar, 20 ml of BASTA (250 mg/ml), and 955 ml of deionized water.

RA sporulation medium was composed per liter of 50 g of succinic acid, 12.1 g of $NaNO_3$, 1 g of glucose, 20 ml of 50× Vogels, and 0.5 ml of a 10 mg/ml $NaMoO_4$ stock solution, pH to 6.0.

STC was composed of 0.8 M sorbitol, 25 mM Tris pH 8, and 25 mM $CaCl_2$.

SPTC was composed of 40% PEG 4000, 0.8 M sorbitol, 25 mM Tris pH 8, and 25 mM $CaCl_2$.

M400 medium was composed per liter of 50 g of maltodextrin, 2 g of $MgSO_4.7H_2O$, 2 g of $KH_2PO_4$, 4 g of citric acid, 8 g of yeast extract, 2 g of urea, 0.5 g of $CaCl_2$, and 0.5 ml of AMG trace metals solution.

M400Da medium was composed per liter of 50 g of maltodextrin, 2 g of $MgSO_4.7H_2O$, 2 g of $KH_2PO_4$, 4 g of citric acid, 8 g of yeast extract, 2 g of urea, and 0.5 ml of AMG trace metals solution. The medium was adjusted to pH 6.0 with 5 N NaOH.

TAE buffer was composed per liter of 4.84 g of Tris Base, 1.14 ml of glacial acetic acid, and 2 ml of 0.5 M EDTA pH 8.0.

Example 1

Fermentation and Mycelial Tissue

*Trichoderma reesei* Tv10 was grown under cellulase inducing conditions. Mycelial samples were harvested and quick-frozen in liquid nitrogen. The samples were stored at −80° C. until they were disrupted for RNA extraction.

Example 2 cDNA Library Construction

Total cellular RNA was extracted from the mycelial samples described in Example 1 according to the method of Timberlake and Barnard (1981, *Cell* 26: 29–37), and the RNA samples were analyzed by Northern hybridization after blotting from 1% formaldehyde-agarose gels (Davis et al., 1986, *Basic Methods in Molecular Biology*, Elsevier Science Publishing Co., Inc., New York). Polyadenylated mRNA fractions were isolated from total RNA with an mRNA Separator Kit™ (Clontech Laboratories, Inc., Palo Alto, Calif.) according to the manufacturer's instructions. Double-stranded cDNA was synthesized using approximately 5 μg of poly(A)+ mRNA according to the method of Gubler and Hoffman (1983, *Gene* 25: 263–269) except a NotI-(dT)18 primer (Pharmacia Biotech, Inc., Piscataway, N.J.) was used to initiate first strand synthesis. The cDNA was treated with mung bean nuclease (Boehringer Mannheim Corporation, Indianapolis, Ind.) and the ends were made blunt with T4 DNA polymerase (New England Biolabs, Beverly, Mass.).

BamHI/EcoRI adaptors were ligated to the blunt ends of the cDNA. After digestion with NotI, the cDNA was size selected by agarose gel electrophoresis (ca. 0.7–4.5 kb), and ligated with pYES2 (Invitrogen Corporation, Carlsbad, Calif.) which had been cleaved with NotI plus BamHI and dephosphorylated with calf-intestine alkaline phosphatase (Boehringer Mannheim Corporation, Indianapolis, Ind.). The ligation mixture was used to transform competent *E. coli* TOP10 cells (Invitrogen Corporation, Carlsbad, Calif.). Transformants were selected on 2YT agar plates (Miller, 1992, *A Short Course in Bacterial Genetics. A Laboratory Manual and Handbook for Escherichia coli and Related Bacteria*, Cold Spring Harbor Press, Cold Spring Harbor, N.Y.) which contained ampicillin at a final concentration of 50 μg per ml.

Example 3

Template Preparation and Nucleotide Sequencing

From the cDNA library described in Example 2, approximately 7000 transformant colonies were picked directly from the transformation plates into 96-well microtiter dishes which contained 100 μl of 2YT broth (Miller, 1992, supra) supplemented with 50 μg of ampicillin per ml. The plates were incubated overnight at 37° C. with shaking. After incubation 100 μl of sterile 50% glycerol was added to each well. The transformants were replicated into secondary, deep-dish 96-well microculture plates (Advanced Genetic Technologies Corporation, Gaithersburg, Md.) containing 1 ml of Magnificent Broth™ (MacConnell Research, San Diego, Calif.) supplemented with 50 μg of ampicillin per ml in each well. The primary microtiter plates were stored frozen at −80° C. The secondary deep-dish plates were incubated at 37° C. overnight with vigorous agitation (300 rpm) on rotary shaker. To prevent spilling and cross-contamination, and to allow sufficient aeration, each secondary culture plate was covered with a polypropylene pad (Advanced Genetic Technologies Corporation, Gaithersburg, Md.) and a plastic microtiter dish cover.

DNA was isolated from each well using the 96-well Miniprep Kit protocol of Advanced Genetic Technologies Corporation (Gaithersburg, Md.) as modified by Utterback et al. (1995, *Genome Sci. Technol.* 1: 1–8). Single-pass DNA sequencing (EST) was done with a Perkin-Elmer Applied Biosystems Model 377 XL Automated DNA Sequencer (Perkin-Elmer/Applied Biosystems, Inc., Foster City, Calif.) using dye-terminator chemistry (Giesecke et al., 1992, *Journal of Virology Methods* 38: 47–60) and the T7 sequencing primer.

Example 4

Analysis of DNA Sequence Data

Nucleotide sequence data were scrutinized for quality, vector sequences and ambiguous base calls at the ends of the DNA sequences were trimmed and all sequences were compared to each other with assistance of PHRED/PHRAP software (University of Washington, Seattle, Wash.). The resulting contigs and singletons were translated in six frames and searched against publicly available protein databases using GeneMatcher™ software (Paracel, Inc., Pasadena, Calif.) with a modified Smith-Waterman algorithm using the BLOSUM 62 matrix.

Example 5

Identification of cDNA Clones Encoding a Family 74 Xyloglucanase

Putative cDNA clones encoding a Family 74 xyloglucanase were identified by comparing the deduced amino acid sequence of the assembled ESTs to protein sequences deposited in publicly available databases such as Swissprot, Genpept, and PIR. Tentative identification was based on amino acid sequence similarity to numerous family 74 cellulases. One clone, *Trichoderma reesei* EST Tr5909, was selected for nucleotide sequence analysis which revealed that the cDNA clone was truncated at its 5 prime end.

Example 6

*Trichoderma reesei* Genomic DNA Extraction

*Trichoderma reesei* strain NRRL 6156 was grown for 8 days at 28° C. and 250 rpm in 25 ml of M400 medium. Mycelia were then collected by filtration through Miracloth (Calbiochem, La Jolla, Calif.) and washed once with 25 ml of 1M Tris pH 8.0) buffer. Excess buffer was drained from the mycelia which were subsequently frozen in liquid nitrogen. The frozen mycelia were ground to a fine powder with a mortar and pestle, and the powder was processed according to the protocol of the DNAeasy Plant Maxi Kit (QIAGEN, Chatsworth, Calif.).

Example 7

Genomic DNA Library Construction, Screening, and Isolation of Genomic Family 74a Clone Genomic libraries of *Trichoderma reesei* strain NRRL 6156 were constructed in λZAP according to the manufac-

49 turer's instructions (Stratagene, La Jolla, Calif.). *Trichoderma reesei* genomic DNA was partially digested with Tsp509I and size-fractionated on 1% agarose gels. DNA fragments migrating in the size range 3–8 kb were excised and eluted from the agarose gel slices using a Qiaquick Gel Purification Kit (QIAGEN, Inc., Chatsworth, Calif.). The eluted DNA fragments were ligated with EcoRI-cleaved and dephosphorylated λZipZap vector arms (Stratagene, La Jolla, Calif.), and the ligation mixtures were packaged using Gigapack III Gold commercial packaging extracts (Stratagene, La Jolla, Calif.). The packaged DNA libraries were plated and amplified in *E. coli* XL10 Blue cells.

The cDNA probe from *Trichoderma reesei* clone Tr5909 was isolated from the vector plasmid and labeled with Digoxigenin-11-dUTP (Boehringer Mannheim, Indianapolis, Ind.) by PCR using the following primers:

```
991423: 5'-GGCCTTGTATCTGACCTATTC-3'  (SEQ ID NO: 3)

991420: 5'-AGGGGTATGTAGCTCTCCTCG-3'  (SEQ ID NO: 4)
```

The resulting 1750 bp PCR fragment was purified by gel electrophoresis and Qiaquick gel purification.

Approximately 45,000 plaques from the library were screened by plaque-hybridization (DIG System, Boehringer Mannheim Corporation, Indianapolis, Ind.) with the Digoxigenin-11-dUTP labeled probe fragment of the *Trichoderma reesei* Tr5909 cDNA clone. Plaques, which gave hybridization signals using CPD-Star (Boehringer Mannheim Corporation, Indianapolis, Ind.) as a substrate, were excised from the plates as agar plugs, and plated in *E. coli* XL10Blue cells so that individual plaques could be isolated. These plaques were screened again by plaque-hybridization with the Digoxigenin-11-dUTP labeled probe fragment of the *Trichoderma reesei* Tr5909 cDNA clone.

The six individual positive clones were subsequently excised from the λZap vector with ExAssist helper phage as pBluscript phagemid (Boehringer Mannheim Corporation, Indianapolis, Ind.). Plasmid DNA was isolated from one clone by passage through *E. coli* SOLR cells (Boehringer Mannheim Corporation, Indianapolis, Ind.) according to the manufacturer's instructions. This clone designated *E. coli* SOLR—pEJG81 was deposited as *E. coli* pEJG81 NRRL B-30502 with the Agricultural Research Service Patent Culture Collection, Northern Regional Research Center, 1815 University Street, Peoria, Ill., 61604, on Jul. 20, 2001.

Example 8

Characterization of the *Trichoderma reesei* Genomic Clone Encoding Family 74 Xyloglucanase DNA sequencing was performed on a Perkin-Elmer Biosystems Model 3700 Automated DNA Sequencer using dye-terminator chemistry (Giesecke et al., 1992, *Journal of Virology Methods* 38: 47–60). Contig sequences were generated using a primer walking strategy. The 8 kb genomic fragment was sequenced to an average redundancy of 3.

The nucleotide sequence and deduced amino acid sequence are shown in FIG. 1. The genomic fragment encodes a polypeptide of 838 amino acids, interrupted by three introns of 59 bp, 50 bp and 59 bp. Using the SignalP software program (Nielsen et al., 1997, *Protein Engineering* 10: 1–6), a signal peptide of 19 residues was predicted. Based on its derived amino acid sequence, the protein can be placed in the glycoside hydrolase Family 74 with its catalytic domain spanning amino acid 20 to 734. Comparison of the deduced amino acid sequence to the Pfam HMM (http://pfam.wustl.edu/hmmsearch.shtml) predicts a fungal cellulose binding domain spanning amino acid 800 to 838. These two domains are separated by a 15 amino acid linker region. Thus, the mature *Trichoderma reesei* xyloglucanase comprises 819 amino acids and a predicted molecular weight of 87.1 kDa.

A comparative alignment of Family 74 glycoside hydrolase sequences using the Clustal W algorithm in the Megalign program of DNA-Star, showed that the deduced amino acid sequence of the *Trichoderma reesei* gene encoding the Family 74 xyloglucanase shares 47% identity with the deduced amino acid sequence of *Aspergillus aculeatus* Avicelase III (SPTREMBL:O74170).

Example 9

Construction of the Family 74 Xyloglucanase Expression Vector

Two synthetic oligonucleotide primers shown below were designed to PCR amplify the *Trichoderma reesei* gene encoding a Family 74 xyloglucanase from pEJG81 for subcloning and expression in a Fusarium host.

```
Forward primer:
                                    (SEQ ID NO: 5)
5'-GGGTCATGAAGGTCTCTCGAGTCCTTG-3'

Reverse primer:
                                    (SEQ ID NO: 6)
5'-GGGTTAATTAATCACACACACTGGTAGTAATC-3'
```

Bold letters represent coding sequence.

In order to facilitate the subcloning of the gene fragment into an expression vector designated pEJG61 (FIG. 2), BspHI and PacI restriction enzyme sites were introduced at the 5' and 3' end of the Family 74 xylanase gene, respectively. The vector pEJG61 contained the *Fusarium venenatum* glucoamylase promoter and *Fusarium oxysporum* trypsin-like protease promoter and terminator (WO 96/00787) as regulatory sequences. The plasmid also contained the bar gene as a selectable marker for fungal transformations (de Block et al., 1987, *EMBO Journal* 6:2513–2518).

Figure 3:
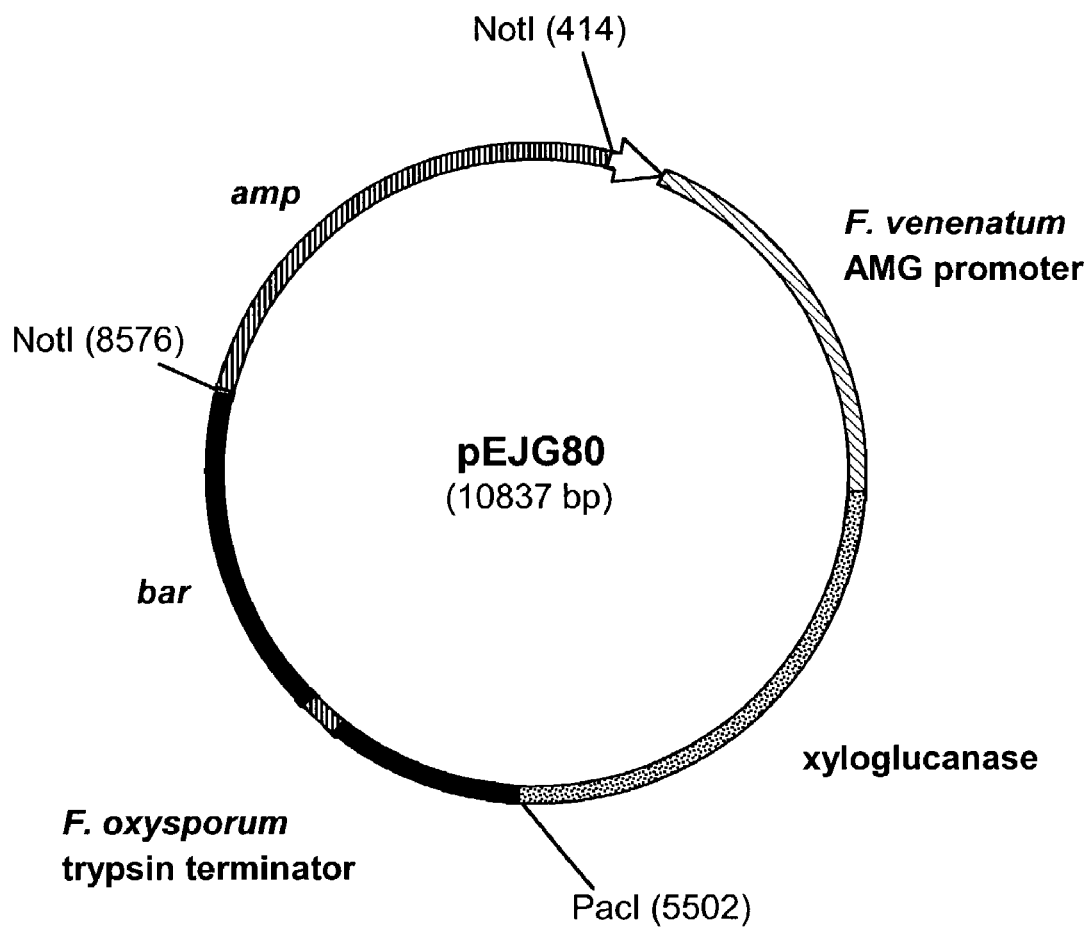
FIG. 3 shows a restriction map of pEJG80.

Fifty picomoles of each of the primers above were used in a PCR reaction containing 200 ng of pEJG81, 1× Taq Buffer (Boehringer Mannheim, Indianapolis, Ind.), 5 µl of 10 mM blend of dATP, dTTP, dGTP, and dCTP, 5 units of Taq (Boehringer Mannheim, Indianapolis, Ind.) and 5 µl DMSO in a final volume of 50 µl. The amplification conditions were one cycle at 94° C. for 2 minutes; 30 cycles at 94° C. for 1 minute, 55° C. for 2 minutes, and 72° C. for 3 minutes; and 1 cycle at 72° C. for 7 minutes. The heat block then went to a 4° C. soak cycle. The amplified DNA fragment of approximately 2.5 kb was purified by gel electrophoresis and a Qiaquick gel purification. The fragment was then subcloned into pCR2.1 TOPO TA cloning vector (Stratagene, La Jolla, Calif.). The clone was digested with restriction endonucleases BspHI and PacI (using conditions specified by the manufacturer). The fragment was purified by gel electrophoresis and Qiaquick gel purification. The cut fragment was cloned into pEJG61 (FIG. 2) that had been previously cut with BspLu11I and PacI resulting in the expression plasmid pEJG80 (FIG. 3) in which transcription of the Family 74 xylanase gene was under the control of the *Fusarium venenatum* glucoamylase promoter. The plasmid pEJG80 was transformed into E. coli XL10 Solopac Gold cells (Stratagene, La Jolla, Calif.). The E. coli transformant containing the pEJG80 plasmid was isolated and plasmid DNA was prepared with the QIAGEN High Speed Maxi Kit (QIAGEN, Inc., Chatsworth, Calif.). pEJG80 was digested with NotI and the vector fragment minus the ampicillin resistant gene was purified by gel electrophoresis and Qiaquick gel purification.

Example 10

Transformation of *Fusarium venenatum* Strain WTY842-1-11

Spores of *Fusarium venenatum* strain WTY842-1-11 (Δtrichodiene synthase, amdS+) a mutant of Fusarium strain A3/5 (ATCC 20334) (Wiebe et al., 1992, *Mycological Research* 96: 555–562; Wiebe et al., 1991, *Mycological Research* 95: 1284–1288; Wiebe et al., 1991, *Mycological Research* 96: 555–562), were generated by inoculating a flask containing 500 ml of RA sporulation medium with 10 plugs from an agar plate containing 6 mg of BASTA™ (Hoechst Schering, Rodovre, Denmark) per ml and incubated at 26.5° C., 150 rpm for 24 hours, then 12 hours, 150 rpm at 28.5° C. Incubation was continued at room temperature for 10 to 14 days. BASTA was extracted twice with phenol:chloroform:isoamyl alcohol (25:24:1), and once with chloroform:isoamyl alcohol (24:1) before use. Spores were harvested through Miracloth and centrifuged 40 minutes at 7000 rpm in a Sorvall RC-5B centrifuge. Pelleted spores were washed twice with sterile distilled water, resuspended in a small volume of water, and then counted using a hemocytometer.

Protoplasts were prepared by inoculating 100 ml of YP (1% yeast extract, 2% bactopeptone, and 5% glucose) medium with $1-2\times10^8$ spores of *Fusarium venenatum* WTY842-1-11 and incubating for 15 hours at 18° C. and 150 rpm. The culture was filtered through Miracloth, washed once with sterile distilled water and once with 1 M $MgSO_4$ and resuspended in 20 ml of 5 mg/ml of NOVOZYME 234™ in 1 M $MgSO_4$. Cultures were incubated at 29° C. and 90 rpm until protoplasts formed. A volume of 30 ml of 1 M sorbitol was added to the protoplast digest and the mixture was centrifuged at 1500 rpm for 10 minutes. The pellet was resuspended, washed twice with 1 M sorbitol, and centrifuged at 1500 rpm for 10 minutes to pellet the protoplasts. Protoplasts were counted with a hemocytometer and resuspended in an 8:2:0.1 solution of STC:SPTC:DMSO to a final concentration of $5\times10^7$ protoplasts/ml. The protoplasts were stored at −80° C., after controlled-rate freezing in a Nalgene Cryo 1° C. Freezing Container.

Two ml of protoplast suspension were added to 100 μg of pEJG28 linear fragment (without the ampicillin resistance gene) in polypropylene tubes (17×100 mm), mixed and incubated on ice for 30 minutes. Two hundred μl of SPTC was mixed gently into the protoplast suspension and incubation was continued at room temperature for 10 minutes. Twenty ml of SPTC was mixed gently into the protoplast suspension and incubation was continued at room temperature for 10 minutes. A 350 ml volume of molten Vogel's $NO_3$ Regeneration Low-Melt medium (cooled to 50° C.) consisting of 50× Vogels with 25 mM $NaNO_3$ stock, 0.8 M sucrose and 1.5% low melting agarose (Sigma Chemical Company, St. Louis, Mo.) was mixed with the protoplasts and then 35 ml were plated onto 100 mm Petri plate containing 35 ml of the identical medium plus 12 mg of BASTA™ per ml. Incubation was continued at room temperature for 10 to 14 days. After two weeks, 50 transformants were apparent. A mycelial fragment from the edge of each transformant was transferred to plates containing Vogel's $NO_3$+BASTA (6 mg/ml) medium. The medium contained 25 g of sucrose, 25 g of Noble agar, 20 ml of 50× Vogel's salts with 25 mM $NaNO_3$ stock, and 6 g of BASTA per liter. The plate was sealed in a plastic bag to maintain moisture and incubated approximately one week at room temperature.

Example 11

Expression of a Family 74 Xyloglucanase Gene

A mycelial fragment from each of the 50 *Fusarium* WTY842-1-11 transformants described in Example 8 was inoculated into 25 ml of M400Da medium. The untransformed host was also run as a control. One ml of culture supernatant was harvested at 4 and 7 days and stored and assayed for xylanase activity as described in Example 12. Both time points showed the presence of xylanase activity.

Example 12

Purification of the Recombinant *Trichoderma reesei* Xyloglucanase

Cultures (day 4) of *Fusarium venenatum* containing the expression plasmid EJG-81, prepared as described in Example 9, were filtered through 0.45 μm nylon membranes (Nalgene, Rochester, N.Y.). The pH of the filtered broth was adjusted to 7.6 by addition of 1 M Tris base. The broth was then loaded at a flow rate of 1.5 ml/minute onto a 2.5×20 cm column containing 100 ml of Avicel PH-101 (FMC, Philadelphia, Pa.) equilibrated with 25 mM Tris pH 7.5 at 4° C. The column was washed with 200 ml of 25 mM Tris pH 7.5 and the xyloglucanase was eluted with ice cold 1% (v/v) triethylamine in deionized water. Elution of protein from the column was monitored by absorbance at 280 nm ($A_{280}$). The fractions containing an $A_{280}$>0.05 were immediately adjusted to pH 7.5 by addition of 1.5 M acetic acid and pooled. The pooled fractions were then concentrated by ultrafiltration (PM-10, Millipore, Bedford, Mass.). The xyloglucanase was further purified by gel filtration on a 16/10 Superdex-200 prep grade column (Amersham Pharmacia Biotech, Inc., Piscataway, N.J.) at a flow rate of 0.75 ml/minute with 25 mM Tris pH 7.5 containing 0.1 M NaCl.

The purified xyloglucanase following Avicel chromatography was estimated to be greater than 95% pure by SDS-PAGE with 8–16% Tris-glycine gels (Invitrogen, Carlsbad, Calif.). The yield of the purified xyloglucanase activity from Avicel chromatography was 98% based on assay with xyloglucan (Tamarind, Megazyme, Ireland) as substrate at pH 6, 40° C. The xyloglucanase assays contained 1 g of xyloglucan (Tamarind, Megazyme, Ireland) per liter of 50 mM sodium acetate pH 5.0 in a final volume of 500 μl. Assays were incubated for 10 minutes at 50° C. and stopped by addition of 125 μl of 0.5N NaOH. Reducing sugars were detected by addition of 300 μl of 15 g/l of p-hydroxybenzoic acid hydrazide containing 0.5 M NaOH and boiling for 10 minutes. The change in absorbance at 410 nm was measured relative to a glucose standard curve.

Example 13

Characterization of the Recombinant *Trichoderma reesei* Xyloglucanase

Native Molecular Weight. The native molecular weight of the xyloglucanase was estimated by Superdex-200 prep grade gel filtration chromatography using a 16×60 cm column at a flow rate of 0.5 ml/minute. Based on comparison to the elution volumes of a standard set of proteins, the xyloglucanase had a calculated molecular weight of 107.7 kDa. This molecular weight is in agreement with the molecular weight of the xyloglucanase estimated from a protein band from purified xyloglucanase electrophoresed in 8–16% Tris-Glycine SDS-PAGE gels (Invitrogen, Carlsbad, Calif.) under reducing conditions. Comparison of both SDS-PAGE and gel filtration chromatography of the xyloglucanase suggest that the protein is a monomer. Additionally, the xyloglucanase contains approximately 20 kDa due to glycosylation, by comparison of the native molecular weight with the molecular weight predicted by primary amino acid sequence.

Substrate Specificity. Stopped-time assays with 5 g of carboxy-methyl cellulose (CMC; Hercules, Wilmington, Del.) per liter, 2 g of phosphoric acid swollen cellulose (PASC) per liter, 5 g of Avicel PH-101 per liter, and 1 g of Tamarind xyloglucan (Megazyme, Bray, Republic of Ireland) per liter were performed by detection of reducing sugars with p-hydroxybenzoic acid hydrazide (PHBAH). Assays were performed in 1 ml of 50 mM sodium acetate pH 5. Reactions were quenched by addition of 250 µl of 0.5 M NaOH, and then centrifuged to remove insoluble substrates. Reducing sugars were detected by transferring 400 µl of quenched reaction supernatant to 200 µl of 1.5% (w/v) PHBAH in 0.5 M NaOH and heating for 10 minutes at 100° C. The absorbance was measured at 410 nm and compared to the absorbance of glucose standards treated identically to samples. Data were corrected for background due to enzyme and substrate reaction with PHBAH.

The substrate specificity of the purified xyloglucanase was determined by measuring of the specific activity on the soluble substrates CMC and PASC, and also the insoluble substrate Avicel. As shown in Table 1, the xyloglucanase had low cellulolytic activity on both soluble and insoluble substrates. However, the xyloglucanase displayed approximately 10-fold higher specific activity toward the hemicellulosic substrate xyloglucan.

TABLE 1

Relative specific activity of the *Trichoderma reesei* xyloglucanase on cellulosic and hemicellulosic substrates.

| Substrate | Relative Specific Activity (relative IU/mg) |
| --- | --- |
| Avicel | 0.007 |
| PASC | 0.04 |
| CMC | 0.089 |
| Xyloglucan | 1.0 |

Thermostability. The thermostability of the xyloglucanase was assessed by pre-incubation at 40°, 50°, 60°, or 70° C. for increasing time intervals followed by CMCase or xyloglucanase assay at room temperature (FIG. 4). CMCase activity was retained for up to 3 hours at both 40 and 50° C., while activity was retained for approximately 15 minutes at 60° C. CMCase activity was not detectable after a 15 minute incubation at 70° C. Xyloglucanase activity increased by approximately 20% over the course of a 3 hour incubation at 40° C. At 50° C., xyloglucanase activity after a 15-minute incubation was approximately 30% higher than the same time period at 40° C. However, after 1 hour at 50° C., xyloglucanase activity dropped to approximately 55% at 3 hours. Incubation for 15 minutes at 60° C. resulted in an approximately 50% loss in xyloglucanase activity, and all xyloglucanase activity was lost by 1 hour at 60° C. All xyloglucanase activity was also lost within 15 minutes at 70° C.

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
| --- | --- | --- |
| *E. coli* pEJG81 | NRRL B-30502 | Jul. 20, 2001 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

SEQUENCE LISTING

<160> NUMBER OF SEQ ID NOS: 6

<210> SEQ ID NO 1
<211> LENGTH: 5698
<212> TYPE: DNA

<213> ORGANISM: Tricoderma reesei

<400> SEQUENCE: 1

```
aattaggagt aggctccgag acagactcta gcagtgtcct cctcctcact gcttcgtcat    60
ttaatcctca tccgaggctc tgtctgagat cgtcacagga ggaggagtga cgaagcagta   120
gaaggtctct cgagtccttg cccttgtcct ggggccgtc atccctgccc atgctgcctt    180
cttccagaga gctcaggaac gggaacagga cccccggcag tagggacggg tacgacggaa   240
ttcatggaag aacgtcaagc tcggcggcgg cggcggcttc gtccccggca tcatcttcca   300
aagtaccttc ttgcagttcg agccgccgcc gccgccgaag caggggccgt agtagaaggt   360
tcccaagaca aaaggcgtag catatgcacg aacagatatt ggcgggctgt accgcctcaa   420
agggttctgt tttccgcatc gtatacgtgc ttgtctataa ccgcccgaca tggcggagtt   480
cgccgacgac tcatggaccg ccgtcacgga tgggattgct gataatgccg gctggcacaa   540
gcggctgctg agtacctggc ggcagtgcct accctaacga ctattacggc cgaccgtgtt   600
ctggggcatc gacgctgttg cgcttgatcc gcaggacgat caaaaggtgt atgccgcagt   660
gaccccgtag ctgcgacaac gcgaactagg cgtcctgcta gttttccaca tacggcgtca   720
cggcatgtat acgaacagct ggtctgtgat gtctctcaga tctagaccta tgattggacg   780
gccgtacata tgcttgtcga ccagacacta cagagagtct agatctggat actaacctgc   840
ctgacattgg ccatatatag ggatccgagt aatggagcca tcattcgctc gtcagaccgc   900
gactgtaacc ggtatatatc cctaggctca ttacctcggt agtaagcgag cagtctggcg   960
ggcgcaacgt ggtccttcac caacttgccc ttcaaagtcg ggggtaacat gccaggacgc  1020
ccgcgttgca ccaggaagtg gttgaacggg aagtttcagc ccccattgta cggtcctgcg  1080
ggagccggag agcgtctggc tgtcgatccg gccaactcca acatcatcta ctttggtgct  1140
cctcggcctc tcgcagaccg acagctaggc cggttgaggt tgtagtagat gaaaccacga  1200
cgctcaggaa acggcctctg gaagtctacg gacggcggcg tgaccttttc caaggtctcg  1260
gcgagtcctt tgccggagac cttcagatgc ctgccgccgc actggaaaag gttccagagc  1320
tcgttcacgg caactgggac gtacatccca gacccgagtg attccaacgg ctacaacagc  1380
agcaagtgcc gttgaccctg catgtagggt ctgggctcac taaggttgcc gatgttgtcg  1440
gacaagcaag gactcatgtg ggttacgttc gactcaacca gcagcacgac cggggagcc   1500
ctgttcgttc ctgagtacac ccaatgcaag ctgagttggt cgtcgtgctg gcccctcgg   1560
acgtctcgta tctttgttgg cacggctgat aacatcactg cttcagtcta tgtgagcacg  1620
tgcagagcat agaaacaacc gtgccgacta ttgtagtgac gaagtcagat acactcgtgc  1680
aatgccggct ccacgtggag tgctgtaccg gggcagccag ggaaatactt tcctcacaag  1740
ttacggccga ggtgcacctc acgacatggc cccgtcggtc cctttatgaa aggagtgttc  1800
gcgaaactgc agccagcaga gaaggccttg tatctgacct attccgatgg cacagggccg  1860
cgctttgacg tcggtcgtct cttccggaac atagactgga taaggctacc gtgtcccggc  1920
tatgatggca cacttggctc agtgtggagg tacgacattg caggggaac ttggaaagac   1980
atactaccgt gtgaaccgag tcacacctcc atgctgtaac gtcccccttg aacctttctg  2040
atcacccctg tctctggatc agatctatac tttggctttg cggccttgg cctcgatttg    2100
tagtggggac agagacctag tctagatatg aaaccgaaac cgccggaacc ggagctaaac  2160
caaaagccag gaacccttgt tgttgcttct ttgaactctt ggtggccaga tgctcagctg  2220
gttttcggtc cttgggaaca acaacgaaga aacttgagaa ccaccggtct acgagtcgac  2280
```

```
tttcggtcga ccgactctgg gacaacatgg agcccgatct gggcgtgggc gagctatccg    2340
aaagccagct ggctgagacc ctgttgtacc tcgggctaga cccgcacccg ctcgataggc    2400
actgagacct attactacag catctcagtg agtcactctt aacgatccga tgcgaatggc    2460
tgactctgga taatgatgtc gtagagtcac tcagtgagaa ttgctaggct acgcttaccg    2520
actgactctg cttcaagact cccaaagcac cgtggatcaa gaacaacttt atcgatgtga    2580
tgactgagac gaagttctga gggtttcgtg gcacctagtt cttgttgaaa tagctacact    2640
cgagcgagtc accgtccgat ggtctcatca agcgcctcgg ctggatgatt gagtctctcg    2700
gctcgctcag tggcaggcta ccagagtagt tcgcggagcc gacctactaa ctcagagagc    2760
agattgaccc aaccgacagc aaccactggc tctacggcac cggaatgaca atctttggcg    2820
tctaactggg ttggctgtcg ttggtgaccg agatgccgtg gccttactgt tagaaaccgc    2880
gccacgatct caccaactgg gacacgcgcc acaatgtgtc aatccaatca ctggcagacg    2940
cggtgctaga gtggttgacc ctgtgcgcgg tgttacacag ttaggttagt gaccgtctgc    3000
gcatcgagga attctccgtc caggacctgg cctctgcacc cggcggaagc gagctattgg    3060
cgtagctcct taagaggcag gtcctggacc ggagacgtgg gccgccttcg ctcgataacc    3120
ccgcagtcgg agacgacaac ggcttcacct ttgccagcag aaacgacctc gggacatcgc    3180
ggcgtcagcc tctgctgttg ccgaagtgga acggtcgtc  tttgctggag ccctgtagcg    3240
cgcagacggt ctgggcaacg cccacatggg ccacctcgac gagcgtcgac tacgccggga    3300
gcgtctgcca gacccgttgc gggtgtaccc ggtggagctg ctcgcagctg atgcggccct    3360
actcggtcaa gagcgtcgtc cgcgtcggca acaccgccgg cacgcaacag gtggccatct    3420
tgagccagtt ctcgcagcag cgcgcagccgt tgtggcggcc gtgcgttgtc accggtaga    3480 cgtccgacgg cggcgcgacg tggagcatcg actacgcggc cgacacgtcc atgaacggcg    3540
gcaggctgcc gccgcgctgc acctcgtagc tgatgcgccg gctgtgcagg tacttgccgc    3600
gcacggtggc ctattcggcc gacggcgaca cgatcctctg gtcgaccgcc tcgtccggcg    3660
cgtgccaccg gataagccgg ctgccgctgt gctaggagac cagctggcgg agcaggccgc    3720
tgcagcgctc gcagttccag ggcagctttg cctccgtctc gagcctgccc gcgggcgccg    3780
acgtcgcgag cgtcaaggtc ccgtcgaaac ggaggcagag ctcggacggg cgcccgcggc    3840
tcatcgcctc ggacaagaag accaacagcg tcttctacgc cggctccgga tcgacctttt    3900
agtagcggag cctgttcttc tggttgtcgc agaagatgcg gccgaggcct agctggaaaa    3960
acgtcagcaa ggacaccggc agcagcttca cgcgcgggcc caagctgggc agcgcaggga    4020
tgcagtcgtt cctgtggccg tcgtcgaagt gcgcgcccgg gttcgacccg tcgcgtccct    4080
cgatccggga tatcgctgct caccgacca  ccgcgggcac gttgtatgtc tcgaccgacg    4140
gctaggccct atagcgacga gtgggctggt ggcgcccgtg caacatacag agctggctgc    4200
tcggcatatt ccgctccaca gactcgggca cgacctttgg ccaagtctcc accgccctga    4260
agccgtataa ggcgaggtgt ctgagcccgt gctggaaacc ggttcagagg tggcgggact    4320
ccaacaccta ccagatcgcc ctgggtgtgg gctcaggctc gaactggaac ctgtatgcct    4380
ggttgtggat ggtctagcgg gacccacacc cgagtccgag cttgaccttg gacatacgga    4440
tcggcaccgg cccgtcaggg gctcgcctct acgccagtga agacagcggc gcctcctgga    4500
agccgtggcc gggcagtccc cgagcggaga tgcggtcacc tctgtcgccg cggaggacct    4560
cggacatcca gggctcccag ggcttcggct ccatcgacag caccaaggtc gccggcagcg    4620
```

-continued

```
gcctgtaggt cccgagggtc ccgaagccga ggtagctgtc gtggttccag cggccgtcgc    4680
gcagcaccgc cgggcaagtc tacgtgggca ccaacgccg gggcgtcttt tacgctcagg     4740
cgtcgtggcg gcccgttcag atgcacccgt ggttgccggc cccgcagaaa atgcgagtcc    4800
gaaccgtcgg cggcggcacg ggcgggactt cctcgtcgac caagcagagc agcagcagta    4860
cttggcagcc gccgccgtgc ccgccctgaa ggagcagctg gttcgtctcg tcgtcgtcat    4920
cctcttccgc cagctcgagc accacgctga ggtcgagcgt tgtatccacg acccgggctt    4980
ggagaaggcg gtcgagctcg tggtgcgact ccagctcgca acataggtgc tgggcccgaa    5040
cgacggtgac ttcgtcgagg accagctcgg ccgccggtcc cacggggtca ggggtcgccg    5100
gctgccactg aagcagctcc tggtcgagcc ggcggccagg gtgccccagt ccccagcggc    5160
gtcattatgc tcagtgcgga gggattgggt ggacggggcc gacgcagtgt gtggcgccgt    5220
cagtaatacg agtcacgcct ccctaaccca cctgccccgg ctgcgtcaca caccgcggca    5280
atgtctgcca gaagcagaat gattgtgagt tgccaccatc tccattagca gcagatcccc    5340
tacagacggt cttcgtctta ctaacactca acggtggtag aggtaatcgt cgtctagggg    5400
cttgactgac tcggccgtca cagattacta ccagtgtgtg tgatgcttga actgccaagc    5460
gaactgactg agccggcagt gtctaatgat ggtcacacac actacgaact tgacggttcg    5520
tcacgaggag agctacatac ccctaggctc gcagtaaaga gctcaagcat ccgaagaagc    5580
agtgctcctc tcgatgtatg gggatccgag cgtcatttct cgagttcgta ggcttcttcg    5640
actagtagta gagatccagt cagataattt gatcatcatc tctaggtcag tctattaa     5698
```

<210> SEQ ID NO 2
<211> LENGTH: 838
<212> TYPE: PRT
<213> ORGANISM: Trichoderma reesei

<400> SEQUENCE: 2

```
Met Lys Val Ser Arg Val Leu Ala Leu Val Leu Gly Ala Val Ile Pro
1               5                   10                  15

Ala His Ala Ala Phe Ser Trp Lys Asn Val Lys Leu Gly Gly Gly Gly
            20                  25                  30

Gly Phe Val Pro Gly Ile Ile Phe His Pro Lys Thr Lys Gly Val Ala
        35                  40                  45

Tyr Ala Arg Thr Asp Ile Gly Gly Leu Tyr Arg Leu Asn Ala Asp Asp
    50                  55                  60

Ser Trp Thr Ala Val Thr Asp Gly Ile Ala Asp Asn Ala Gly Trp His
65                  70                  75                  80

Asn Trp Gly Ile Asp Ala Val Ala Leu Asp Pro Gln Asp Asp Gln Lys
                85                  90                  95

Val Tyr Ala Ala Val Gly Met Tyr Thr Asn Ser Trp Asp Pro Ser Asn
            100                 105                 110

Gly Ala Ile Ile Arg Ser Ser Asp Arg Gly Ala Thr Trp Ser Phe Thr
        115                 120                 125

Asn Leu Pro Phe Lys Val Gly Gly Asn Met Pro Gly Arg Gly Ala Gly
    130                 135                 140

Glu Arg Leu Ala Val Asp Pro Ala Asn Ser Asn Ile Ile Tyr Phe Gly
145                 150                 155                 160

Ala Arg Ser Gly Asn Gly Leu Trp Lys Ser Thr Asp Gly Gly Val Thr
                165                 170                 175

Phe Ser Lys Val Ser Ser Phe Thr Ala Thr Gly Thr Tyr Ile Pro Asp
            180                 185                 190
```

```
Pro Ser Asp Ser Asn Gly Tyr Asn Ser Asp Lys Gln Gly Leu Met Trp
        195                 200                 205

Val Thr Phe Asp Ser Thr Ser Thr Thr Gly Gly Ala Thr Ser Arg
210                 215                 220

Ile Phe Val Gly Thr Ala Asp Asn Ile Thr Ala Ser Val Tyr Val Ser
225                 230                 235                 240

Thr Asn Ala Gly Ser Thr Trp Ser Ala Val Pro Gly Gln Pro Gly Lys
                245                 250                 255

Tyr Phe Pro His Lys Ala Lys Leu Gln Pro Ala Glu Lys Ala Leu Tyr
                260                 265                 270

Leu Thr Tyr Ser Asp Gly Thr Gly Pro Tyr Asp Gly Thr Leu Gly Ser
                275                 280                 285

Val Trp Arg Tyr Asp Ile Ala Gly Gly Thr Trp Lys Asp Ile Thr Pro
290                 295                 300

Val Ser Gly Ser Asp Leu Tyr Phe Gly Phe Gly Gly Leu Gly Leu Asp
305                 310                 315                 320

Leu Gln Lys Pro Gly Thr Leu Val Val Ala Ser Leu Asn Ser Trp Trp
                325                 330                 335

Pro Asp Ala Gln Leu Phe Arg Ser Thr Asp Ser Gly Thr Thr Trp Ser
                340                 345                 350

Pro Ile Trp Ala Trp Ala Ser Tyr Pro Thr Glu Thr Tyr Tyr Tyr Ser
                355                 360                 365

Ile Ser Thr Pro Lys Ala Pro Trp Ile Lys Asn Asn Phe Ile Asp Val
                370                 375                 380

Thr Ser Glu Ser Pro Ser Asp Gly Leu Ile Lys Arg Leu Gly Trp Met
385                 390                 395                 400

Ile Glu Ser Leu Glu Ile Asp Pro Thr Asp Ser Asn His Trp Leu Tyr
                    405                 410                 415

Gly Thr Gly Met Thr Ile Phe Gly Gly His Asp Leu Thr Asn Trp Asp
                420                 425                 430

Thr Arg His Asn Val Ser Ile Gln Ser Leu Ala Asp Gly Ile Glu Glu
                435                 440                 445

Phe Ser Val Gln Asp Leu Ala Ser Ala Pro Gly Gly Ser Glu Leu Leu
            450                 455                 460

Ala Ala Val Gly Asp Asp Asn Gly Phe Thr Phe Ala Ser Arg Asn Asp
465                 470                 475                 480

Leu Gly Thr Ser Pro Gln Thr Val Trp Ala Thr Pro Thr Trp Ala Thr
                485                 490                 495

Ser Thr Ser Val Asp Tyr Ala Gly Asn Ser Val Lys Ser Val Val Arg
                500                 505                 510

Val Gly Asn Thr Ala Gly Thr Gln Gln Val Ala Ile Ser Ser Asp Gly
            515                 520                 525

Gly Ala Thr Trp Ser Ile Asp Tyr Ala Ala Asp Thr Ser Met Asn Gly
            530                 535                 540

Gly Thr Val Ala Tyr Ser Ala Asp Gly Asp Thr Ile Leu Trp Ser Thr
545                 550                 555                 560

Ala Ser Ser Gly Val Gln Arg Ser Gln Phe Gln Gly Ser Phe Ala Ser
                565                 570                 575

Val Ser Ser Leu Pro Ala Gly Ala Val Ile Ala Ser Asp Lys Lys Thr
                580                 585                 590

Asn Ser Val Phe Tyr Ala Gly Ser Gly Ser Thr Phe Tyr Val Ser Lys
                595                 600                 605
```

-continued

```
Asp Thr Gly Ser Ser Phe Thr Arg Gly Pro Lys Leu Gly Ser Ala Gly
610                 615                 620

Thr Ile Arg Asp Ile Ala Ala His Pro Thr Thr Ala Gly Thr Leu Tyr
625                 630                 635                 640

Val Ser Thr Asp Val Gly Ile Phe Arg Ser Thr Asp Ser Gly Thr Thr
            645                 650                 655

Phe Gly Gln Val Ser Thr Ala Leu Thr Asn Thr Tyr Gln Ile Ala Leu
            660                 665                 670

Gly Val Gly Ser Gly Ser Asn Trp Asn Leu Tyr Ala Phe Gly Thr Gly
            675                 680                 685

Pro Ser Gly Ala Arg Leu Tyr Ala Ser Gly Asp Ser Gly Ala Ser Trp
690                 695                 700

Thr Asp Ile Gln Gly Ser Gln Gly Phe Gly Ser Ile Asp Ser Thr Lys
705                 710                 715                 720

Val Ala Gly Ser Gly Ser Thr Ala Gly Gln Val Tyr Val Gly Thr Asn
            725                 730                 735

Gly Arg Gly Val Phe Tyr Ala Gln Gly Thr Val Gly Gly Thr Gly
            740                 745                 750

Gly Thr Ser Ser Ser Thr Lys Gln Ser Ser Ser Thr Ser Ser Ala
            755                 760                 765

Ser Ser Ser Thr Thr Leu Arg Ser Ser Val Val Ser Thr Thr Arg Ala
770                 775                 780

Ser Thr Val Thr Ser Ser Arg Thr Ser Ser Ala Ala Gly Pro Thr Gly
785                 790                 795                 800

Ser Gly Val Ala Gly His Tyr Ala Gln Cys Gly Gly Ile Gly Trp Thr
            805                 810                 815

Gly Pro Thr Gln Cys Val Ala Pro Tyr Val Cys Gln Lys Gln Asn Asp
            820                 825                 830

Tyr Tyr Tyr Gln Cys Val
            835
```

<210> SEQ ID NO 3
<211> LENGTH: 21
<212> TYPE: DNA
<213> ORGANISM: Trichoderma reesei

<400> SEQUENCE: 3
ggccttgtat ctgacctatt c                    21

<210> SEQ ID NO 4
<211> LENGTH: 21
<212> TYPE: DNA
<213> ORGANISM: Trichoderma reesei

<400> SEQUENCE: 4 agggtatgt agctctcctc g                     21

<210> SEQ ID NO 5
<211> LENGTH: 27
<212> TYPE: DNA
<213> ORGANISM: Trichoderma reesei

<400> SEQUENCE: 5
gggtcatgaa ggtctctcga gtccttg              27

```
<210> SEQ ID NO 6
<211> LENGTH: 32
<212> TYPE: DNA
<213> ORGANISM: Trichoderma reesei

<400> SEQUENCE: 6
gggttaatta atcacacaca ctggtagtaa tc                                    32
```

What is claimed is:

1. An isolated polypeptide having Family 74 xyloglucanase activity,
    having the amino acid sequence of SEQ ID NO: 2 or amino acids 20 to 838 of SEQ ID NO: 2.

2. The polypeptide of claim 1, comprising the amino acid sequence of SEQ ID NO: 2.

3. The polypeptide of claim 2, consisting of the amino acid sequence of SEQ ID NO: 2.

4. The polypeptide of claim 3, which consists of amino acids 20 to 838 of SEQ ID NO: 2.

5. The polypeptide of claim 1, which is encoded by the nucleic acid sequence contained in plasmid pEJG81 which is contained in *E. coli* NRRL B-30502.

6. A detergent composition comprising the polypeptide of claim 1.

7. A process for machine treatment of fabrics which process comprises treating fabric during a washing cycle of a machine washing process with a washing solution containing the polypeptide of claim 1.

* * * * *